(12) United States Patent
Wessels et al.

(10) Patent No.: US 8,473,051 B1
(45) Date of Patent: Jun. 25, 2013

(54) LOW-ENERGY ATRIAL CARDIOVERSION THERAPY WITH CONTROLLABLE PULSE-SHAPED WAVEFORMS

(75) Inventors: Richard J. Wessels, Scandia, MN (US); Igor R. Efimov, Wildwood, MO (US); Wenwen Li, St. Louis, MO (US)

(73) Assignee: Cardialen, Inc., St. Louis, MO (US)

( * ) Notice: Subject to any disclaimer, the term of this patent is extended or adjusted under 35 U.S.C. 154(b) by 0 days.

(21) Appl. No.: 13/340,637

(22) Filed: Dec. 29, 2011

Related U.S. Application Data

(60) Provisional application No. 61/428,098, filed on Dec. 29, 2010.

(51) Int. Cl.
*A61N 1/00* (2006.01)
(52) U.S. Cl.
USPC .............................................. 607/7
(58) Field of Classification Search
USPC .............................................. 607/7
See application file for complete search history.

(56) References Cited

U.S. PATENT DOCUMENTS

| | | | |
|---|---|---|---|
| 3,729,008 A | 4/1973 | Berkovits |
| 3,738,370 A | 6/1973 | Charms |
| 3,942,536 A | 3/1976 | Mirowski et al. |
| 4,136,703 A | 1/1979 | Wittkampf |
| 4,384,585 A | 5/1983 | Zipes |
| 4,727,877 A | 3/1988 | Kallok |
| 4,768,512 A | 9/1988 | Imran |
| 5,107,834 A | 4/1992 | Ideker et al. |
| 5,184,616 A | 2/1993 | Weiss |
| 5,199,429 A | 4/1993 | Kroll et al. |
| 5,265,600 A | 11/1993 | Adams et al. |
| 5,275,621 A | 1/1994 | Mehra |
| 5,282,836 A | 2/1994 | Kreyenhagen et al. |
| 5,306,291 A | 4/1994 | Kroll et al. |

(Continued)

FOREIGN PATENT DOCUMENTS

| | | |
|---|---|---|
| EP | 0 393 265 A1 | 10/1990 |
| EP | 1 062 971 A1 | 12/2000 |

(Continued)

OTHER PUBLICATIONS

Peters et al., "Disturbed Connexin43 Gap Junction Distribution Correlates With the Location of Reentrant Circuits in the Epicardial Border Zone of Healing Canine Infarcts That Cause Ventricular Tachycardia," Circulation, 1997, 95:988-996, USA.

(Continued)

*Primary Examiner* — George Manuel
(74) *Attorney, Agent, or Firm* — Patterson Thuente Pedersen, P.A.

(57) ABSTRACT

An implantable therapy generator that includes sensing circuitry that senses cardiac signals representative of atrial activity and ventricular activity; detection circuitry connected to the sensing circuitry; control circuitry that controls generation and selective delivery of a multi-stage atrial cardioversion therapy to implanted electrodes, each stage of the therapy including multiple pulses, each pulse including multiple high-frequency sub-pulses; and therapy circuitry. The therapy circuitry includes a high-voltage charging circuit charging a storage capacitor to a predetermined voltage; a delivery capacitor connectable to the storage capacitor; and a control circuit adapted to selectively cause the storage capacitor to be electrically connected to the delivery capacitor so as to charge the delivery capacitor to a predetermined delivery voltage, and to cause a delivery switching circuit to be repeatedly opened and closed at a predetermined rate, thereby causing the sub-pulses to be transmitted to the electrodes.

2 Claims, 19 Drawing Sheets

U.S. PATENT DOCUMENTS

| | | | |
|---|---|---|---|
| 5,330,509 A | 7/1994 | Kroll et al. | |
| 5,334,219 A | 8/1994 | Kroll | |
| 5,365,391 A | 11/1994 | Sugiyama et al. | |
| 5,372,605 A | 12/1994 | Adams et al. | |
| 5,383,907 A | 1/1995 | Kroll | |
| 5,387,613 A | 2/1995 | Goldberg et al. | |
| 5,391,186 A | 2/1995 | Kroll et al. | |
| 5,403,356 A | 4/1995 | Hill et al. | |
| 5,405,363 A | 4/1995 | Kroll et al. | |
| 5,407,444 A | 4/1995 | Kroll | |
| 5,413,591 A | 5/1995 | Knoll | |
| 5,433,729 A | 7/1995 | Adams et al. | |
| 5,449,377 A | 9/1995 | Adams et al. | |
| 5,489,293 A | 2/1996 | Pless et al. | |
| 5,545,182 A | 8/1996 | Stotts et al. | |
| 5,545,204 A | 8/1996 | Cammilli et al. | |
| 5,562,708 A | 10/1996 | Combs et al. | |
| 5,620,464 A | 4/1997 | Kroll et al. | |
| 5,620,468 A | 4/1997 | Mongeon et al. | |
| 5,674,248 A | 10/1997 | Kroll et al. | |
| 5,676,687 A | 10/1997 | Ayers | |
| 5,683,429 A | 11/1997 | Mehra | |
| 5,713,924 A * | 2/1998 | Min et al. | 607/4 |
| 5,722,995 A | 3/1998 | Olson et al. | |
| 5,766,226 A | 6/1998 | Pedersen | |
| 5,782,876 A | 7/1998 | Flammang | |
| 5,792,187 A | 8/1998 | Adams | |
| 5,797,967 A | 8/1998 | KenKnight | |
| 5,813,999 A | 9/1998 | Ayers et al. | |
| 5,840,079 A | 11/1998 | Warman et al. | |
| 5,925,066 A | 7/1999 | Kroll et al. | |
| 5,928,270 A | 7/1999 | Ramsey, III | |
| 5,995,871 A | 11/1999 | Knisley | |
| 6,070,081 A | 5/2000 | Takahashi et al. | |
| 6,081,746 A | 6/2000 | Pendekanti et al. | |
| 6,085,116 A | 7/2000 | Pendekanti et al. | |
| 6,085,119 A | 7/2000 | Scheiner et al. | |
| 6,091,991 A | 7/2000 | Warren | |
| 6,094,596 A | 7/2000 | Morgan | |
| 6,157,859 A | 12/2000 | Alt | |
| 6,178,351 B1 | 1/2001 | Mower | |
| 6,185,459 B1 | 2/2001 | Mehra et al. | |
| 6,205,357 B1 | 3/2001 | Ideker et al. | |
| 6,233,483 B1 | 5/2001 | Causey, III et al. | |
| 6,246,906 B1 | 6/2001 | Hsu et al. | |
| 6,292,691 B1 | 9/2001 | Pendekanti et al. | |
| 6,327,500 B1 | 12/2001 | Cooper et al. | |
| 6,330,477 B1 * | 12/2001 | Casavant | 607/14 |
| 6,463,330 B1 | 10/2002 | Rabinovitch et al. | |
| 6,510,342 B1 | 1/2003 | Park et al. | |
| 6,526,317 B2 | 2/2003 | Hsu et al. | |
| 6,556,862 B2 | 4/2003 | Hsu et al. | |
| 6,567,698 B2 | 5/2003 | Herleikson | |
| 6,587,720 B2 | 7/2003 | Hsu et al. | |
| 6,711,442 B1 | 3/2004 | Swerdlow et al. | |
| 6,745,081 B1 | 6/2004 | Helland et al. | |
| 6,763,266 B1 | 7/2004 | Kroll | |
| 6,813,516 B2 | 11/2004 | Ujhelyi et al. | |
| 6,847,842 B1 | 1/2005 | Rodenhiser et al. | |
| 6,937,896 B1 | 8/2005 | Kroll | |
| 7,006,867 B1 | 2/2006 | Kroll | |
| 7,020,517 B2 | 3/2006 | Weiner | |
| 7,047,071 B2 | 5/2006 | Wagner et al. | |
| 7,079,891 B1 | 7/2006 | Kroll | |
| 7,110,811 B2 | 9/2006 | Wagner et al. | |
| 7,113,822 B1 | 9/2006 | Kroll | |
| 7,120,490 B2 | 10/2006 | Chen et al. | |
| 7,127,292 B2 | 10/2006 | Warman et al. | |
| 7,139,611 B1 | 11/2006 | Kroll et al. | |
| 7,142,927 B2 | 11/2006 | Benser et al. | |
| 7,142,928 B2 | 11/2006 | Sharma et al. | |
| 7,155,286 B1 | 12/2006 | Kroll et al. | |
| 7,181,276 B1 | 2/2007 | Province et al. | |
| 7,194,304 B1 | 3/2007 | Bornzin et al. | |
| 7,480,351 B2 | 1/2009 | Hiatt, Jr. et al. | |
| 2002/0128565 A1 | 9/2002 | Rudy | |
| 2003/0083727 A1 | 5/2003 | Casavant et al. | |
| 2003/0220676 A1 | 11/2003 | Helland | |
| 2004/0111123 A1 | 6/2004 | Ware et al. | |
| 2004/0220641 A1 | 11/2004 | Wagner et al. | |
| 2005/0096701 A1 | 5/2005 | Donovan et al. | |
| 2005/0154420 A1 | 7/2005 | Diaz et al. | |
| 2006/0161206 A1 | 7/2006 | Efimov et al. | |
| 2007/0021793 A1 | 1/2007 | Voegele et al. | |
| 2007/0088395 A1 | 4/2007 | Province et al. | |
| 2009/0062877 A1 | 3/2009 | Krinski et al. | |
| 2009/0204164 A1 | 8/2009 | Efimov et al. | |
| 2010/0016917 A1 | 1/2010 | Efimov et al. | |
| 2011/0009916 A1 | 1/2011 | Efimov et al. | |
| 2011/0029032 A1 | 2/2011 | Bardy et al. | |

FOREIGN PATENT DOCUMENTS

| | | |
|---|---|---|
| GB | 2 025 236 A | 1/1980 |
| WO | WO 96/11035 | 4/1996 |
| WO | WO 2006/042295 A1 | 4/2006 |
| WO | WO 2008/063498 A1 | 5/2008 |

OTHER PUBLICATIONS

Niemann et al., "Intracardiac Voltage Gradients during Transthoracic Defibrillation: Implications for Postshock Myocardial Injury," Acad. Emerg. Med., Feb. 2005, 12(2):99-105, USA.

Kodama et al., "Aftereffects of high-intensity DC stimulation of the electromechanical performance of ventricular muscle", Am J. Physiol., 1994, 267:H248-H258, USA.

Li et al., "Defribillation Shocks Produce Different Effects on Purkinje Fibers and Ventricular Muscle: Implications for Successful Defibrillation, Refibrillation and Postshock Arrhythmia", J Am Coll Cardiol, 1993, 22:607-614, USA.

Zhou et al., "Epicardial Mapping of Ventricular Defibrillation With Monophasic and Biphasic Shocks in Dogs," Circulation Research, Jan. 1993, 72(1):145-160, USA.

Li et al., "Mechanisms of enhanced shock-induced arrhythmogenesis in the rabbit heart with healed myocardial infarction," Am. J. Physiol. Heart Circ Physiol., May 3, 2005, 289:H1054-H1068, USA.

Sambelashvili et al., "Nonlinear effects in subthreshold virtual electrode polarization," Am. J. Physiol. Heart Circ, Physiol., 2003, 284(6):H2368-H2374, USA.

Aguel et al., "Advances in Modeling Cardiac Defibrillation," Int'l Journal of Bifurcation & Chaos, 2003, 13(12):3791-3803, USA.

Hillebrenner et al., "Postshock arrhythmogenesis in a slice of the canine heart," J. Cardiovasc. Electrophys., 2003, 14:S249-S256, USA.

Trayanova et al., "Virtual Electrode-Induced Positive and Negative Graded Responses: New Insights into Fibrillation Induction and Defibrillation," J. Cardiovascular Electrophysiology, 2003, 14(7):756-763, USA.

Larson et al., "Analysis of Electrically-Induced Reentrant Circuits in a Sheet of Myocardium," Annals Biomed. Eng., 2003, 31:768-780, USA.

Efimov, "Filbrillatin or Neurillation: Back to the future in our concepts of sudden cardiac death?", Circ. Res., May 30, 2003, 92(10):1062-1064, USA.

Efimov et al., "Diastolic Shocking Experience: Do Virtual Anodes Exist Only During Systole?", J. Cardiovascular Electrophysiology, Nov. 2003, 14(11):1223-1224, USA.

Efimov et al., Fast Fluorescent Mapping of Electrical Activity in the Heart: Practical Guide to Experimental Design and Applications, Chapter 7, pp. 131-156, USA, 2003.

Cheng et al., "Shock-induced arrhythmogenesis is enhanced by 2,3-butanedione monoxime compared with cytochalasin D," Am. J. Physiol. Heart Circ. Physiol., 2004, 286:H310-H318, USA.

Takagi et al., "Unpinning and Removal of a Rotating Wave in Cardiac Muscle", Phys. Review Letters, Jul. 30, 2004, 93(5):058101-1-058101-4, USA.

Li et al., "Effects of Lidocaine on Shock-Induced Vulnerability", J. Cardiovascular Electrophysiology, Oct. 2003, 14(10):S237-S248, USA.

Cheng et al., "Mechanisms of Shock-Induced Arrhythmogenesis During Acute Global Ischemia", Am J Physiol. Heart Circ. Physiol., Jun. 2002, 282(6)H2141-51, USA.

Qu et al., "Mechanisms of Superiority of Ascending Ramp Waveforms: New Insights into Mechanisms of Shock-induced Vulnerability and Defibrillation," Am. J. Physiol. Heart Circ. Physiol., 2005, 289:H569-H577, USA.

Ashihara et al., "Spiral Wave Control by a Localized Stimulus: A Bidomain Model Study," J. Cardiovascular Electrophysiology, Feb. 2004 15(2):226-233, USA.

Ramanathan, "Noninvasive electrocardiographic imaging for cardiac electrophysiology and arrhythmia," Nature Medicine, Apr. 2004, 10(4):422-428, USA.

Nikolski et al., "Fluorescent Imaging of a Dual-Pathway Atrioventricular-Nodal Conduction System," Circ Res., Feb. 16, 2001, pp. 1-7, USA.

Qu et al., "The Gurvich waveform has lower defibrillation threshold than the Zoll waveform and the truncated exponential waveform in the rabbit heart," Can. J. Physiol. Pharmacol., 2005, 83:152-160, USA.

Grosu et al., "Learning and Detecting Emergent Behavior in Networks of Cardiac Myocytes", Communications of the ACM, Mar. 2009, pp. 97-104, vol. 52, No. 3, USA.

Ripplinger et al., "Mechanisms of unpinning and termination of ventricular tachycardia", Am J. Physiol. Heart Circ. Physiol., 2006, pp. H184-H192, USA Sepulveda et al., "Current injection into a two-dimensional anisotropic bidomain", Biophys. J., vol. 55, May 1989, pp. 987-999, USA.

Allessie et al., "Regional Control of Atrial Fibrillation by Rapid Pacing in Conscious Dogs", Circulation, vol. 84, No. 4, Oct. 1991, pp. 1689-1697, USA.

Daoud et al., "Response of Type I Atrial Fibrillation to Atrial Pacing in Humans", Circulation, vol. 94, No. 5, 1996, 13 pages, USA.

Disertori et al., "Antitachycardia pacing therapies to terminate atrial tachyarrhythmias: the AT500 Italian Registry", European Heart Journal Supplements, 2001, pp. 16-24, USA.

Pumir et al., "Unpinning of a Rotating Wave in Cardiac Muscle by an Electric Field", J. Theor. Biol., vol. 199, 1999, pp. 311-319, USA.

Ladwig et al., "Absence of an Impact of Emotional Distress on the Perception of Intracardiac Shock Discharges," International Journal of Behavioral Medicine, 2003, 10(1):56-65, USA.

Fishler et al., "Spatiotemporal Effects of Syncytial Heterogeneities on Cardiac Far-field Excitations during Monophasic and Biphasic Shocks", Journal of Cardiovascular Electrophysiolgy, 1998, 9(12):1310-24, USA.

Efimov et al., "Virtual Electrode-Induced Phase Singularity: A Basic Mechanism of Defibrillation Failure," Circulation Research, 1998, 82(8):918-25, USA.

Efimov et al., "Transmembrane Voltage Changes Produced by Real and Virtual Electrodes During Monophasic Defibrillation Shock Delivered by an Implantable Electrode," Journal of Cardiovascular Electrophysiolgy, 1997, 8(9):1031-45, USA.

Cheng et al., "Virtual Electrode-Induced Reexcitation: A Mechanism of Defibrillation," Circulation Research, 1999, 85(11):1056-66, USA.

Fishler, "Syncytial Heterogeneity as a Mechanism Underlying Cardiac Far-Field Stimulation During Defibrillation-Level Shocks," Journal of Cardiovascular Electrophysiolgy, 1998, 9(4):384-94, USA.

Tsukerman et al., "Defibrillation of the Heart by a Rotating Current Field," Kardiologiia, 1973, 13(12):75-80, USA.

Zheng et al., "Reduction of the Internal Atrial Defibrillation Threshold with Balanced Orthogonal Sequential Shocks," Journal of Cardiovascular Electrophysiolgy, 2002; 13(9):904-9, USA.

Hucker et al., "Atrioventricular conduction with and without AV nodal delay: two pathways to the bundle of His in the rabbit heart", Am J. Physiol. Heart Circ. Physiol., 2007, 293:H1122-H1130, USA.

Mowrey et al., "Membrane Time Constant During Internal Defibrillation Strength Shocks in Intact Heart: Effects of $Na^+$ and $Ca^{2+}$ Channel Blockers," J. Cardiovascular Electrophysiology, Apr. 25, 2004, Jun. 8, 2008 and Jan. 2009, 20(1):85-92, USA.

Cartee et al., "The Transient Subthreshold Response of Spherical and Cylindrical Cell Models to Extracellular Stimulation", IEEE Trans. Biomed. Eng., vol. 39, No. 1, Jan. 1992, pp. 76-85.

Ideker et al., "Correlation Among Fibrillation, Defibrillation and Cardiac Pacing", Pacing Clin. Electrophysiol., vol. 18, Mar. 1995, pp. 512-525.

Sobie et al., "A Generalized Activating Function for Predicting Virtual Electrodes in Cardiac Tissue", Biophys. J., vol. 73, Sep. 1997, pp. 1410-1423.

Trayanova et al., "The Response of a Spherical Heart to a Uniform Electric Field: A Bidomain Analysis of Cardiac Stimulation", J. IEEE trans. Biomed. Eng., vol. 40, No. 9, Sep. 1993, pp. 899-908.

Davidenko et al., "Stationary and drifting spiral waves of excitation in isolated cardiac muscle," Nature, vol. 355, pp. 349-351, Jan. 23, 1992.

Gray et al., "Spatial and temporal organization during cardiac fibrillation," Nature, vol. 392, pp. 75-78, May 14, 1998.

Witkowski et al, "Spatiotemporal evolution of ventricular fibrillation," Nature, vol. 392, pp. 78-82, Mar. 5, 1998.

Cherry et al., "Visualization of spiral and scroll waves in simulated and experimental cardiac tissue", New J. Phys., vol. 10, pp. 125016-125059, 2008.

Koster et al., "A randomized trial comparing monophasic and biphasic waveform shocks for external cardioversion of atrial fibrillation," Am. Heart. J. vol. 147, pp. e1-e7, 2004.

Babbs et al., "Therapeutic indices for transchest defibrillator shocks: Effective, damaging, and lethal electrical doses," Am. Heart J., vol. 99, No. 6, pp. 734-738, Jun. 1980.

Santini et al., "Single Shock Endocavitary Low Energy Intracardiac Cardioversion of Chronic Atrial Fibrillation," J. Interv. Card. Electrophysiol., vol. 3, pp. 45-51, 1999.

Sakurai et al., "Design and Control of Wave Propagation Patterns in Excitable Media," Science, vol. 296, pp. 2009-2012, Jun. 14, 2002.

Rappel et al, "Spatiotemporal Control of Wave Instabilities in Cardiac Tissue," Phys. Rev. Lett., vol. 83, No. 2, pp. 456-459, Jul. 12, 1999.

Fenton et al., "Multiple mechanisms of spiral wave breakup in a model of cardiac electrical activity," Chaos, vol. 12, No. 3, pp. 852-892, Sep. 2002.

Fenton et al., "Vortex dynamics in three-dimensional continuous myocardium with fiber rotation: Filament instability and fibrillation," Chaos, vol. 8, No. 1, pp. 20-47, Mar. 1998.

MacKenzie, "Making sense of a heart gone wild," Science, vol. 303, pp. 786-787, Feb. 6, 2004.

Walcott et al., "Do clinically relevant transthoracic defibrillation energies cause myocardial damage and dysfunction?" Resuscitation, vol. 59, pp. 59-70, 2003.

Fenton et al., "Termination of Atrial Fibrillation Using Pulsed Low-Energy Far-Field Stimulation," Circulation, vol. 120, pp. 467-476, 2009.

Plonsey, "The Nature of Sources of Bioelectric and Biomagnetic Fields," Biophys. J., vol. 39, pp. 309-312, 1982.

Fast et al., "Activation of Cardiac Tissue by Extracellular Electrical Shocks: Formation of 'Secondary Sources' at Intercellular Clefts in Monolayers of Cultured Myocytes," Circ. Res., vol. 82, pp. 375-385, 1998.

Sambelashvili et al., "Virtual electrode theory explains pacing threshold increase caused by cardiac tissue damage," Am. J. Physiol. Heart Circ. Physiol., vol. 286, pp. H2183-H2194, 2004.

Hooks et al, "Cardiac Microstructure: Implications for Electrical Propagation and Defibrillation in the Heart," Circ. Res., vol. 91, pp. 331-338, 2002.

Trayanova et al., "Modeling Defibrillation: Effects of Fiber Curvature," J. Electrocardiol., vol. 31 (suppl.), pp. 23-29, 1998.

Roth et al., "A Bidomain Model for the Extracellular Potential and Magnetic Field of Cardiac Tissue," IEEE Trans. Biomed. Eng., vol. 33, No. 4, pp. 467-469, Apr. 1986.

Murray, "The Physiological Principle of Minimum Work: I. The Vascular System and the Cost of Blood Volume," Proc. Natl. Acad. Sci. USA, vol. 12, pp. 207-214, 1926.

Kassab, "Scaling laws of vascular trees: of form and function," Am. J. Physiol. Heart Circ. Physiol., vol. 290, pp. H894-H903, 2006.

Maleckar et al., "Polarity reversal lowers activation time during diastolic field stimulation of the rabbit ventricles: insights into mechanisms," Am. J. Physiol. Heart Circ. Physiol., vol. 295, pp. H1626-H1633, 2008.

Kirchhof et al, "Regional entrainment of Atrial Fibrillation Studied by High-Resolution Mapping in Open-Chest Dogs," Circulation, vol. 88, pp. 736-749, 1993.

Pumir et al, "Wave Emission from Heterogeneities Opens a Way to Cotnrolling Chaos in the Heart," Phys. Rev. Lett., vol. 99, pp. 208101-1, 2007.

Gray et al, "Termination of spiral waves during cardiac fibrillation via shock-induced phase resetting," Proc. Natl. Acad. Sci. USA, vol. 102, No. 13, pp. 4672-4677, Mar. 29, 2005.

Gressard et al., "Pacing Lead/Myocardium Interface: Modeling and Characterization of the Impedance", Computers in Cardiology, vol. 32, pp. 901-903, 2005.

International Preliminary Report on Patentability for International Application No. PCT/US2005/040187 dated Feb. 24, 2009, 6 pages.

International Search Report for International Application No. PCT/US2007/023836 dated Apr. 9, 2008, 7 pages.

Korean Intellectual Property Office, PCT Written Opinion for International Application No. PCT/US2008/086483, dated Jun. 25, 2009, 14 pages.

Supplementary Partial European Search Report for European Application No. 08858734.0, dated Nov. 17, 2011, 11 pages.

PCT International Search Report dated Jan. 17, 2012, 4 pages.

PCT Written Opinion dated Jan. 17, 2012, 4 pages.

Written Opinion of the International Searching Authority for International Application No. PCT/US2008/086483, dated Jun. 25, 2009, 7 pages.

European Patent Office, European Office Action for European Application No. 05825356.8, dated Oct. 5, 2009, 6 pages, Munich, Germany.

PCT Application No. PCT/US2012/072046, filed Dec. 28, 2012, PCT International Search Report dated Apr. 25, 2013, 3 pages.

* cited by examiner

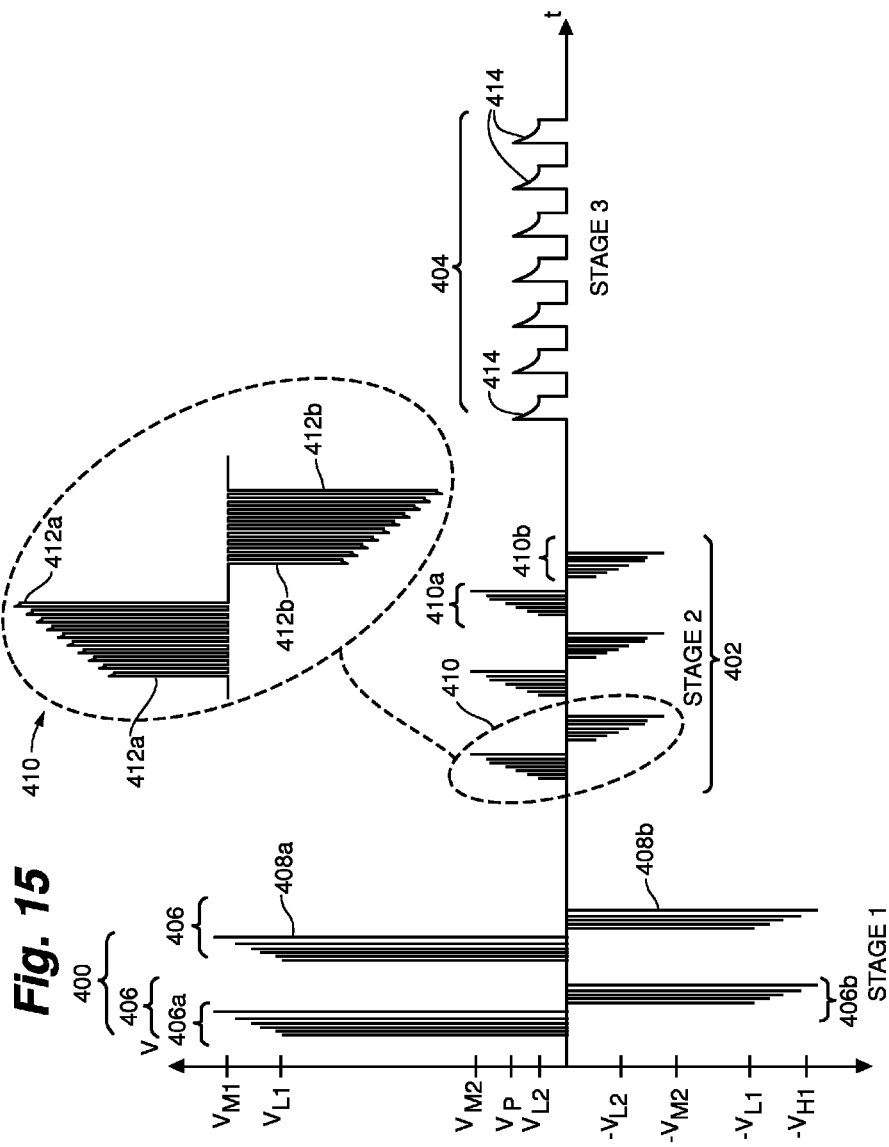

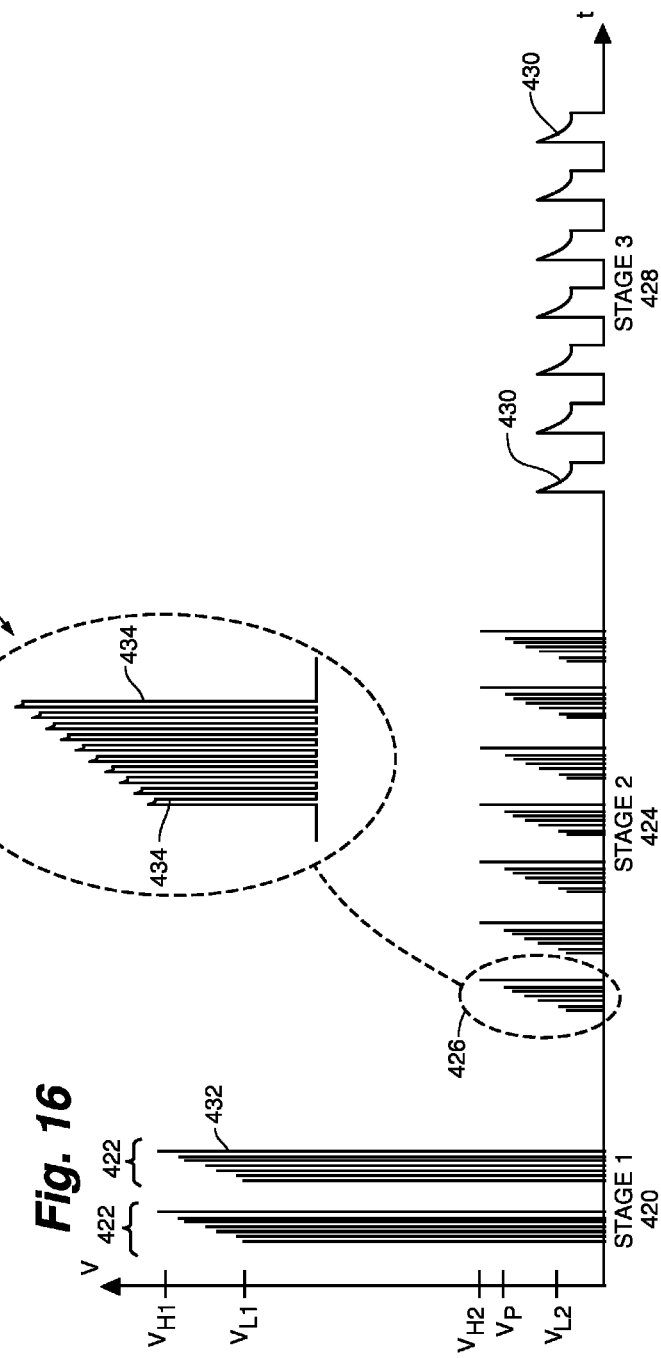

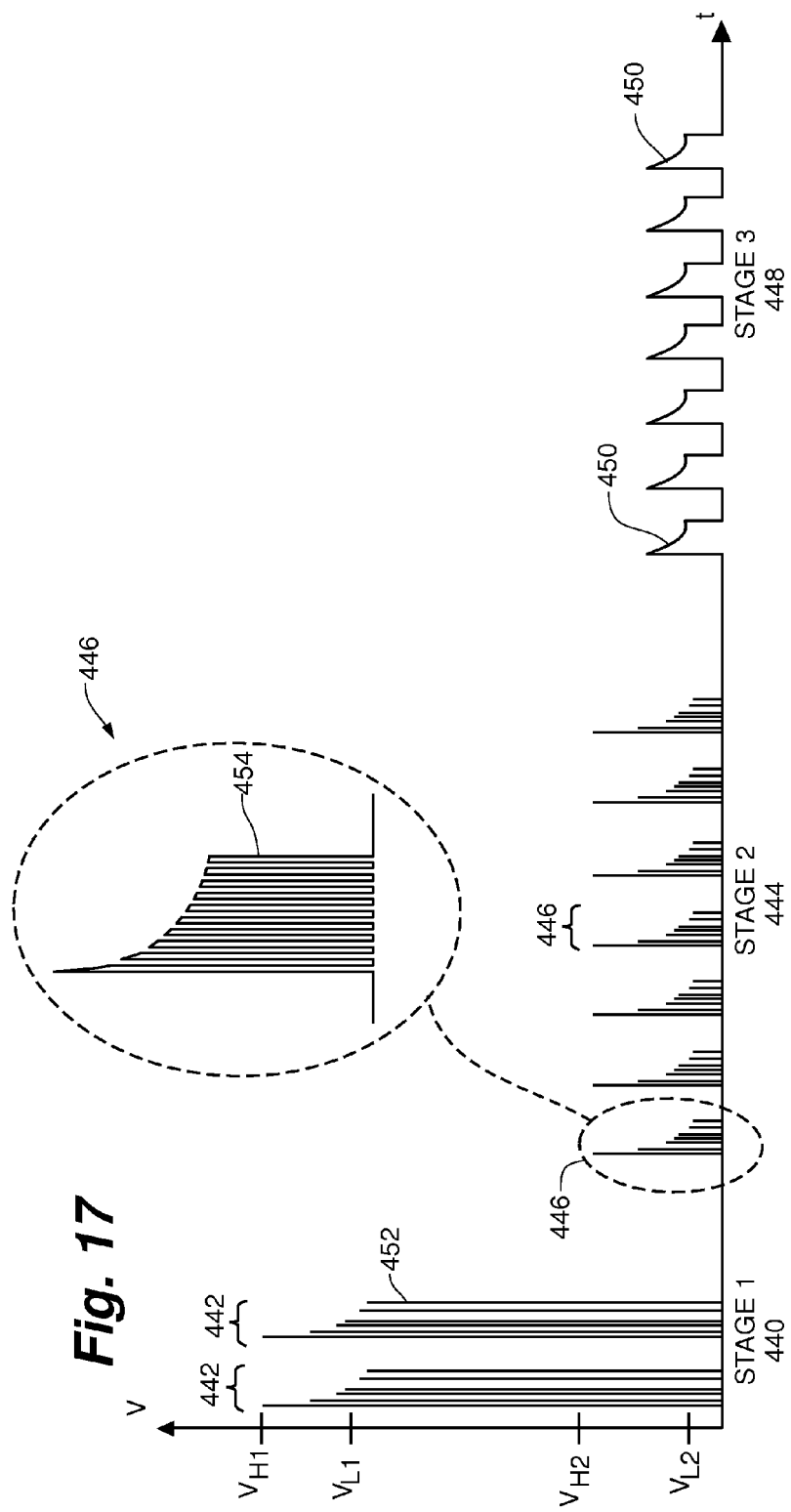

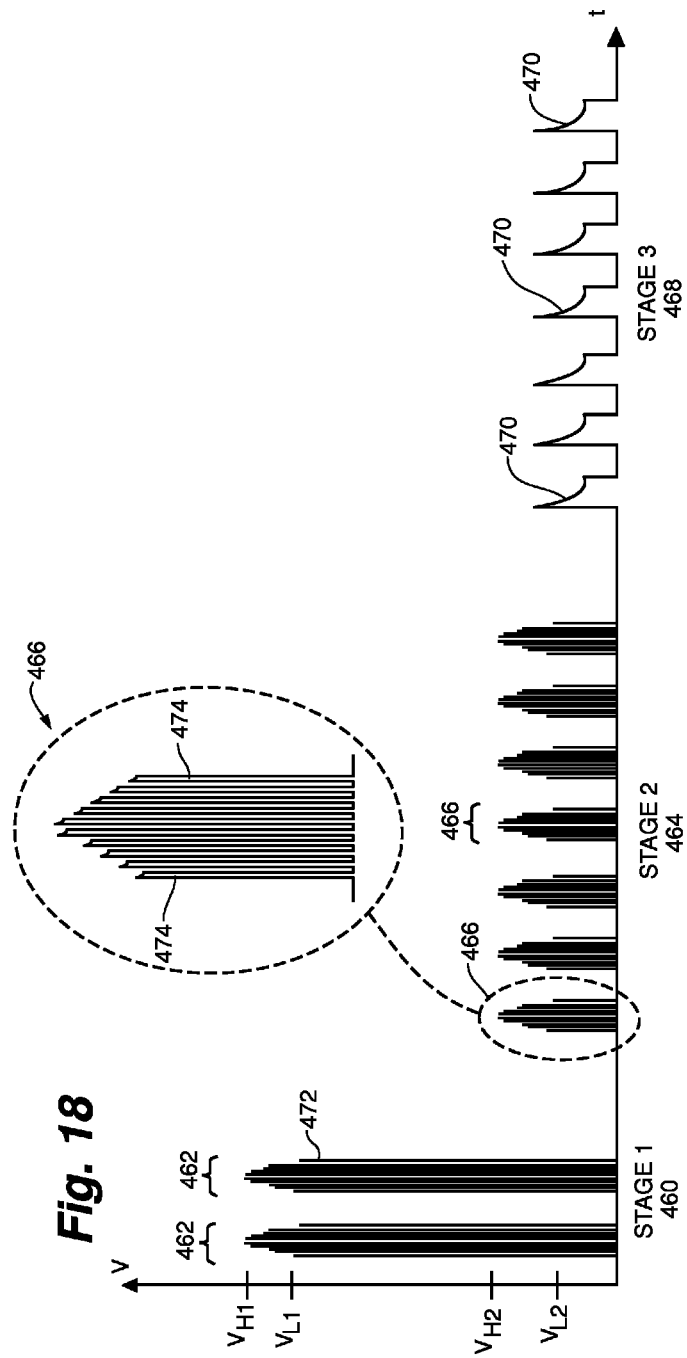

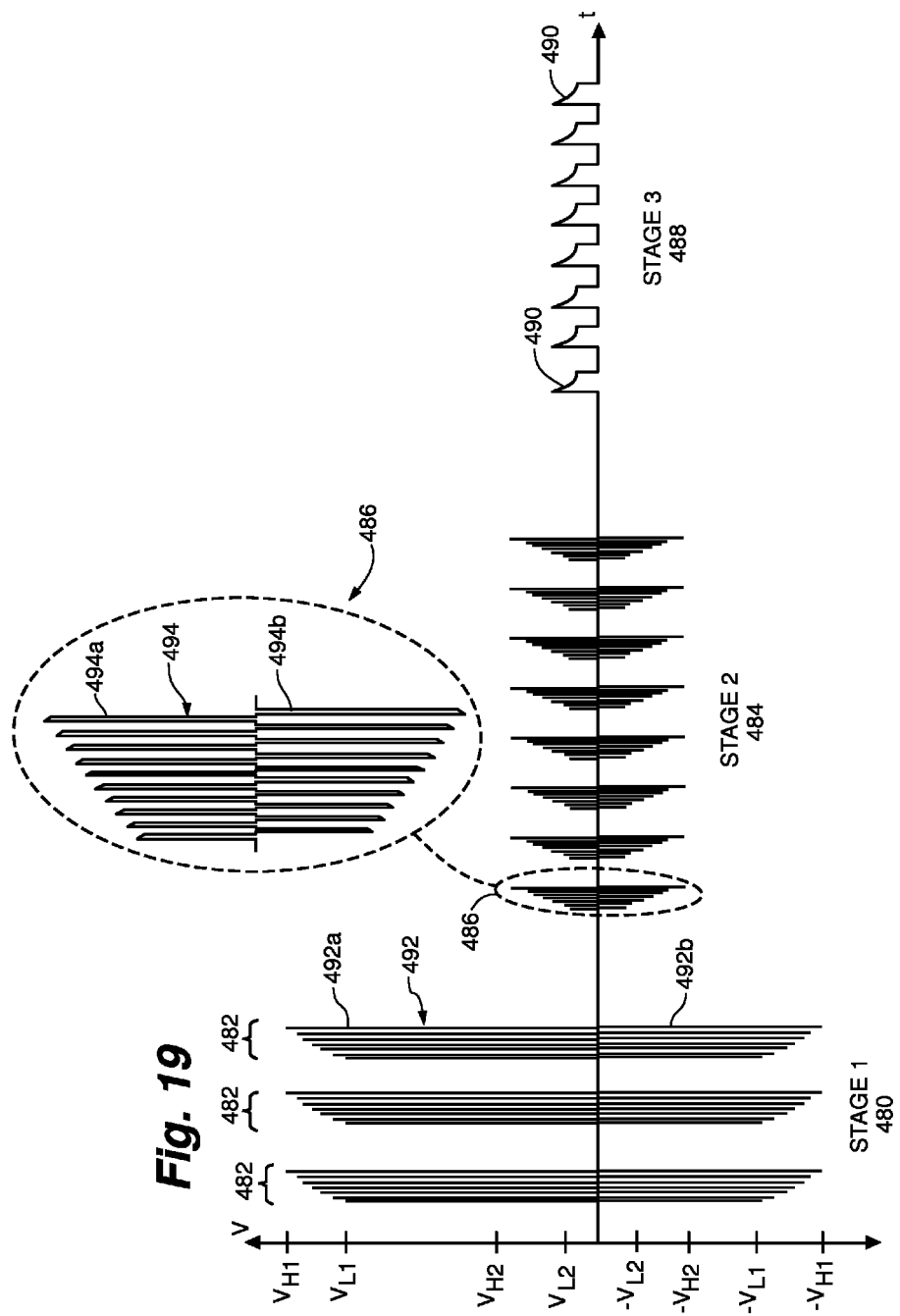

LOW-ENERGY ATRIAL CARDIOVERSION THERAPY WITH CONTROLLABLE PULSE-SHAPED WAVEFORMS

RELATED APPLICATION

The present application claims the benefit of U.S. Provisional Application No. 61/428,098 filed Dec. 29, 2010, which is incorporated herein in its entirety by reference.

FIELD OF THE INVENTION

The present disclosure relates generally to the treatment of atrial tachyarrhythmias, such as atrial fibrillation. More particularly, the present disclosure relates to devices and methods of using low-energy electrical stimuli from a device that delivers atrial cardioversion therapy comprised of a controllable high-frequency, pulsed waveshape to minimize patient sensation and a combination of multiple pulsed waveshapes to destabilize and extinguish reentry mechanisms that maintain AF.

BACKGROUND OF THE INVENTION

Atrial fibrillation ("AF") is the most prevalent arrhythmia in clinical practice and a major contributor to morbidity and mortality. While some suffering from atrial fibrillation may experience no symptoms, those who do have atrial fibrillation symptoms may experience palpitations, which are sensations of a racing, uncomfortable, irregular heartbeat or a flopping in the chest, decreased blood pressure, weakness, lightheadedness, confusion, shortness of breath or chest pain, some of which may be rehabilitating. A recent study estimated that the number of Americans afflicted by AF will increase from the current range of 2.2 to 5.6 million to more than 12 million by 2050. This increase will be driven significantly by demographics, since AF affects nearly 4% of the U.S. population over 60 years of age. The enormity of the clinical problem is magnified by well-described sequelae: thromboembolic stroke, congestive heart failure (CHF), increased mortality and cognitive dysfunction. According to a recent report by the AF Stat™ working group, AF costs Medicare more than $15.7 billion annually due to costly complications. As the population continues to age, partially because of better therapies for atherosclerosis and heart failure, and becomes increasingly overweight, AF will become more prevalent, and its effect on morbidity and mortality will become even more important.

Although several milestones in the clinical management of AF have been met and many therapy options exist for AF, none fully meets the need of the large and growing patient base. Rhythm and rate control drugs represent typical first-line therapy but these are ineffective in significant numbers of patients. In addition, antiarrhythmic drugs in particular often have serious side effects. Anticoagulant drugs, administered to reduce the elevated risk of stroke, also have significant side effects, lack of efficacy in some patients, and compliance problems.

Conventional non-pharmacologic treatments of AF, such as external cardioversion, require costly patient hospitalization and anesthesia, and are frequently ineffective in that the arrhythmia concerned may recur within 12 months. Surgical ablation, whether performed on an open-chest or minimally-invasive basis, along with other surgical procedures such as excision of the left atrial appendage, carry their own risks and meet the needs of only a limited patient population. Newer left atrial appendage closure devices, approved for use in specified patients to reduce the potential generation of emboli, do not address the underlying condition and only address a portion of the patient population.

There have been many advances in catheter ablation techniques and these have brought significant advantages to the field. However, catheter ablations are still tedious procedures; and involve significant risks, which include cardiac perforation, esophageal injury, embolism, phrenic nerve injury, and pulmonary vein stenosis. In addition, recurrence 12 months after catheter ablation is reported in 5 to 10% of cases and has recently been reported in a range of 15% to 25% in different patient groups when follow-up is extended to around five years.

Implantable devices have been developed solely for AF therapy, and have generally fallen into five groups: atrial defibrillators, atrial burst stimulators, parasympathetic nerve stimulators, ventricular rate stabilization pacemakers and drug dispensers. The use of implantable atrial cardioverters (IACs) has previously been tried in patients with recurrent persistent AF. Although initial clinical trials of such early IAC devices indicated that they had high specificity and sensitivity to AF and delivered safe and effective shocks, they did not gain patient acceptance. This was primarily due to the fact that, given the technology employed at the time, the energy level needed to achieve cardioversion (~3.0 J) greatly exceeded the pain threshold, causing great discomfort in patients who then opted to forego continued therapy.

For example, a first generation IAC, developed by InControl, was trialed in patients in the early 1990s. It was shown to provide prompt and safe restoration of sinus rhythm in patients with recurrent tachyarrhythmias. But it was not introduced to the market; primarily because patients could not tolerate the discomfort caused by the shocks which required approximately 3 Joules using conventional biphasic truncated exponential (BTE) shock therapy. Prior attempts to reduce the shock energy and voltage by providing pulsed waveforms, including ascending or other modified waveforms resulted in modest improvements, but these concepts were difficult to implement economically or physically in implantable devices.

SUMMARY OF THE INVENTION

The present invention comprises devices for, and methods of, delivering low energy, pain-free shocks targeted against AF. The devices and methods convert atrial fibrillation to normal sinus rhythm using novel waveforms, algorithms, and leads at energy levels that will not be perceived by the patient. Low-energy, biphasic electrical stimuli, delivered in a multi-pulse, unique controllable waveform by the device delivers unpinning therapy that destabilizes, terminates and suppresses the reentry mechanism known to maintain AF, until natural sinus rhythm reemerges as the dominate atrial rhythm.

In an embodiment, the present invention comprises an atrial arrhythmia treatment apparatus. The apparatus includes a signal multiplexing and protection portion including a plurality of leads and a multiplexer, an EGM sensing and arrhythmia determination portion in communication with the signal muxing and protection portion, and a therapy voltage generation and delivery portion in communication with the signal muxing and protection portion. The therapy voltage generation and delivery portion includes a pulse generator delivering one or more low-energy, controllable pulse-shaped waveforms to convert the atrial arrhythmia.

In another embodiment, the present invention comprises a method of treating an atrial arrhythmia. The method includes implanting an atrial arrhythmia device of the present invention into a patient, configuring the atrial arrhythmia treatment device in the patient, and causing the atrial arrhythmia treatment device to apply a pulse-shaped atrial cardioversion therapy to the patient in response to detection of an atrial arrhythmia or in response to a natural person initiating therapy.

In yet another embodiment, the present invention comprises a compact implantable defibrillator that includes a pulse generator outputting a plurality of high-frequency pulses of controllable amplitude and duration so as to deliver any variety of non-traditional, low-energy therapy waveforms to the patient, including ascending and descending pulsed waveforms. The pulse generator includes a plurality of high voltage transistors to form an H-bridge to deliver bipolar therapy pulses to the heart. In an embodiment, the time constant formed by a portion of heart capacitance and resistance determines the off time of a switching circuit of the generator.

BRIEF DESCRIPTION OF THE DRAWINGS

The invention may be more completely understood in consideration of the following detailed description of various embodiments of the invention in connection with the accompanying drawings, in which:

FIG. 15 depicts a three-stage therapy waveform with ascending, biphasic pulses as provided by the therapy voltage generation and delivery system of the present invention;

FIG. 16 depicts a three-stage therapy waveform with ascending, monophasic pulses as provided by the therapy voltage generation and delivery system of the present invention;

FIG. 17 depicts a three-stage therapy waveform with descending, non-linear monophasic pulses as provided by the therapy voltage generation and delivery system of the present invention;

FIG. 18 depicts a three-stage therapy waveform with peaked, monophasic pulses as provided by the therapy voltage generation and delivery system of the present invention; and FIG. 19 depicts a multi-stage therapy waveform with biphasic sub-pulses forming the pulses of each therapy stage.

Figure 1:
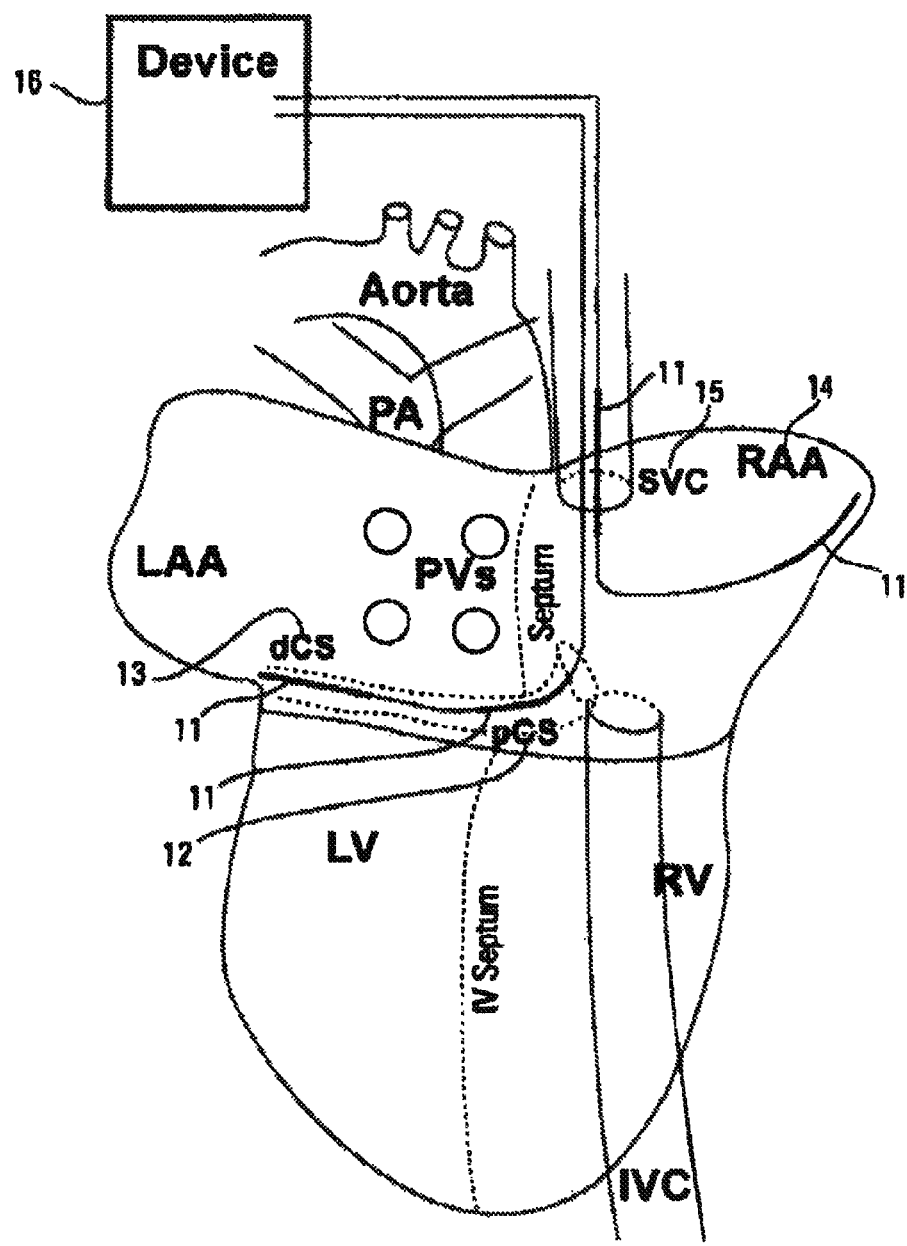
FIG. 1 depicts a schematic posterior view of a human heart and anatomical locations of implantable defibrillation leads and sensing electrodes.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention as defined by the appended claims.

DETAILED DESCRIPTION

The present invention provides an enhanced atrial defibrillator system, which is intended for human use as an implantable device. The system is designed for delivery of multi-stage electrical-shock therapy, each stage of the therapy comprising multiple pulses, and each pulse comprising multiple, high-frequency sub-pulses. The duration and amplitude of the high-frequency sub-pulses can be varied to produce optimally-shaped pulse waveforms, while the overall energy delivered remains below an energy threshold perceived as painful. Electrical circuits generating and delivering such therapy may include a primary storage capacitor supplied by a charging circuit, and a secondary delivery capacitor charged by the primary storage capacitor. Charging of the secondary delivery capacitor by the primary supply capacitor is switchably controlled to determine sub-pulse voltage amplitude, while high-speed switching of the delivery capacitor determines sub-pulse duration so as to deliver one or more high-frequency pulse-shaped waveforms to a patient. An effective atrial defibrillator or pulse therapy generator that successfully employs such circuits to deliver energy in the form of controllable waveform shock pulses which are sufficiently great to effect the conversion of the tachyarrhythmia and sufficiently low so as not to effect sensation of pain in the patient will be a valuable new class of implantable device delivering a new type of therapy, in addition to existing implantable devices such as dual chamber pacemakers and defibrillators.

Pain thresholds depend on many factors, including autonomic tone, presence of drugs, placement of electrodes, voltage levels and shock-pulse waveforms. However, endocardial cardioversion shock energies greater than 1 J may not be tolerated by the patient. The pain threshold is generally considered to be 1 J. Termination of AF with energy levels <1 J was associated with little, if any, discomfort in a study conducted by Murgatroyd, et al. Thus, there is an acute need for implantable AF treatment devices that enable successful cardioversion without exceeding pain thresholds for the typical patient.

Most research in lowering the atrial defibrillation threshold (DFT) has concentrated largely on the electrodes used or the waveforms delivered. It has been demonstrated that paroxysmal or acute AF has a significantly lower DFT than that of persistent or chronic AF. With the advent of a commercially-viable IAC, the timing of first shock pulse delivery relative to AF onset may be a major determinant of defibrillation efficacy and energy required. Therefore, greater use of IACs could significantly reduce the number of patients progressing from acute to chronic AF.

With the present invention, AF internal conversion to normal sinus rhythm is possible using voltage levels that will not be perceived by the patient. Low-voltage shock pulses, applied as monophasic or biphasic waveforms, can induce virtual electrode polarization (VEP) at anatomical heterogeneities, which can be used to destabilize and halt reentrant circuits.

Virtual electrode polarization (VEP) builds upon the observation that heterogeneities (anatomical obstacles such as pulmonary veins) can serve as anchors for errant circuits and effectively "pin" or "anchor" reentry arrhythmias, thus allowing the errant circuit to stabilize. These heterogeneities serve as "virtual electrodes", concentrating maximum tissue depolarization at the point where the errant circuit has stabilized. Test data in vitro and in vivo demonstrate that low-voltage shocks, applied as biphasic waveforms in phase-synchronized multiple pulses in conjunction with far-field entrainment approach, induces VEP at these heterogeneities and enables a novel approach to atrial defibrillation. The average energy required for internal cardioversion in the canine vagally-mediated AF model is equal to 0.1 J.

Phase-dependent, low voltage multiple pulses comprised of multiple, high-frequency sub-pulses, having energy below single pulse defibrillation thresholds and above current magnitudes for anti-tachycardia pacing, as delivered by embodiments of the present invention and applied on a far field basis to unpin reentry and errant circuits pinned to heterogeneities, achieve significant reductions of voltage and energy levels required for atrial defibrillation. In other embodiments, such therapy may be applied on a near-field, or other basis.

In an embodiment, the low-energy shock pulses incorporate phased unpinning therapy comprising multiple pulses of between 0.02 and 0.1 J, delivered through multiple electrodes, so as to generate a virtual electrode polarization or rotating field. A variety of electrode placement configurations may be utilized.

Figure 2:
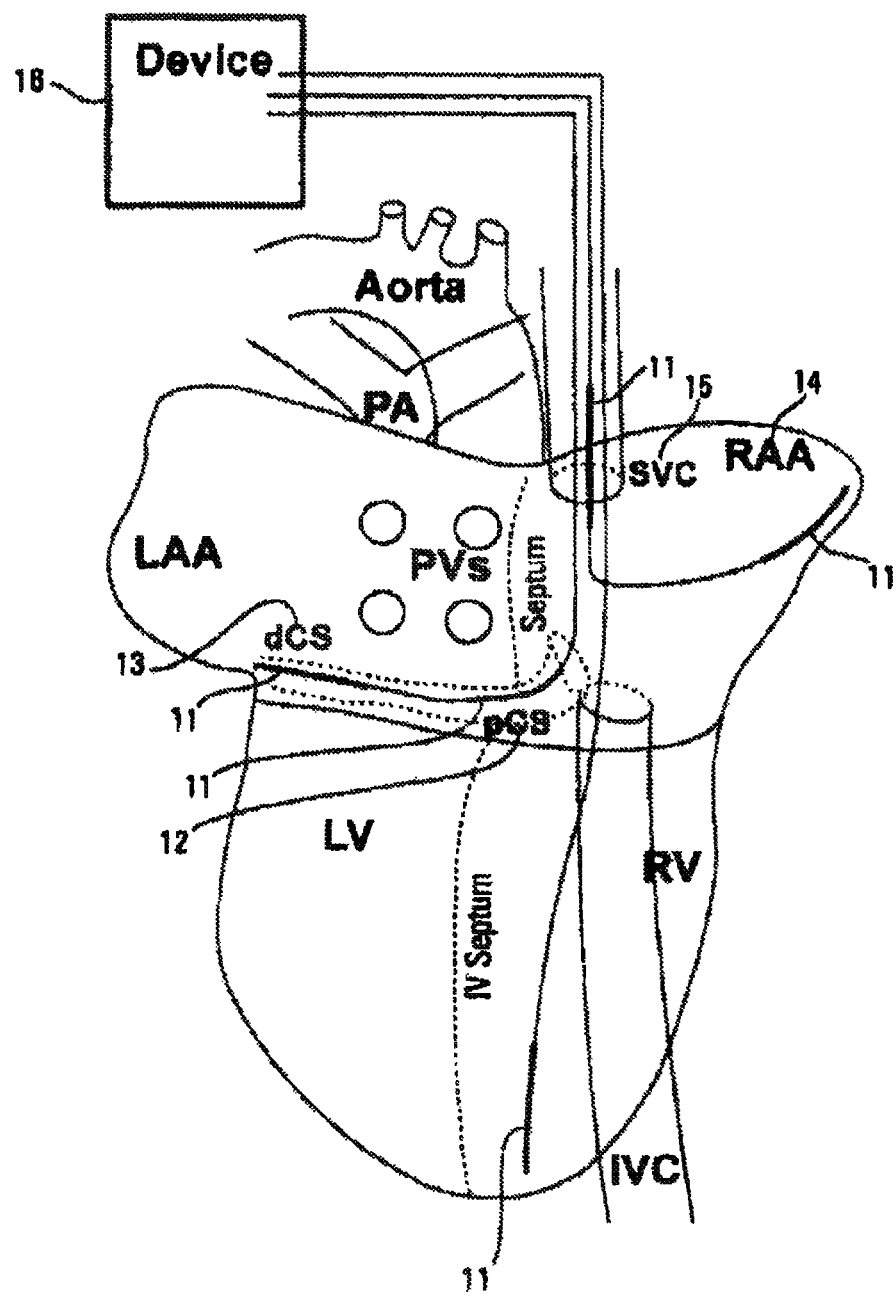
FIG. 2 depicts a schematic posterior view of a human heart and anatomical locations of implantable defibrillation leads and sensing electrodes with an optional lead placed in the right ventricle.

Referring to FIGS. 1 and 2, various field configurations can be achieved by placing several implantable defibrillation electrodes 11 into the proximal 12 and distal 13 coronary sinus ("CS"), the right appendage ("RAA") 14, and the superior venae cavae ("SVC") 15. In one aspect, a right ventricular lead is positioned as part of the implantation (FIG. 2). In another aspect, no ventricular lead is positioned (FIG. 1), removing the need to cross a heart valve during lead implantation. Leads may be active or passive fixation. In an embodiment, and as depicted in FIGS. 1 and 2, no leads are placed in the left side of the heart, thus reducing the time required for implantation.

Electric fields can be delivered between any two of these electrodes as well as between one of these electrodes and the device itself 16 (hot can configuration). Modulation of the electric field vector can be used to achieve maximum coverage of the entire atria and to maintain optimal Virtual Electrode Polarization pattern through the entire cycle of arrhythmia in order to depolarize the maximum area of excitable gaps. The optimal electric fields used and the correct sequence of fields can also be explored on a trial and error basis for each patient or can be estimated based on external information regarding potential sites of the reentrant circuits, or can be based on a combination of both.

Figure 3:
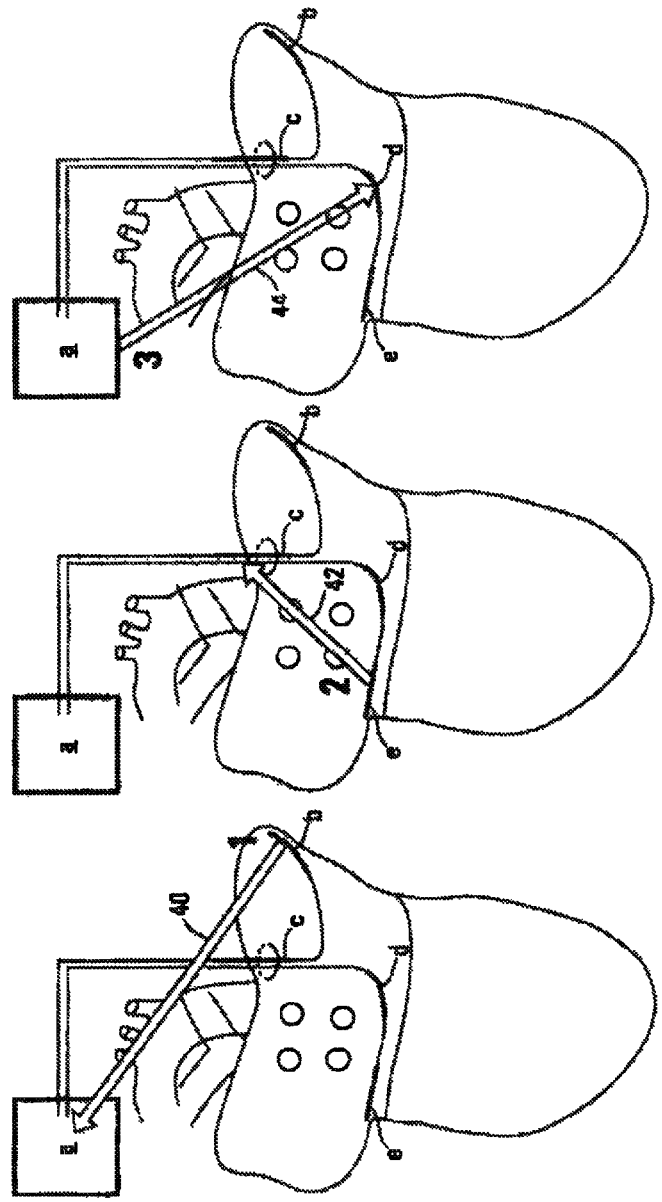
FIG. 3A depicts a simplified schematic posterior view of a human heart, anatomical locations of implantable defibrillation leads and electrodes, and the direction of a first shock/pulse train.
FIG. 3B depicts a simplified schematic posterior view of a human heart, anatomical locations of implantable defibrillation leads and electrodes, and the direction of a second shock/pulse train.
FIG. 3C depicts a simplified schematic posterior view of a human heart, anatomical locations of implantable defibrillation leads and electrodes, and the direction of a third shock/pulse train.

FIGS. 3A, 3B and 3C together depict a clock-wise rotation of the vectors of a series of three consecutive far field unpinning shocks or pulses. Each shock can be comprised of a train of electrical pulses. In this example, multiple, monophasic shocks can be applied with intervals as a function of arrhythmia cycle length. In one example, the far field unpinning shocks can be square waves, 10 ms in duration of which the voltage and vectors will be varied to determine minimum termination voltage. In other embodiments, the far field unpinning shocks or pulses may be rounded, staggered, ascending, descending, biphasic, multiphasic or variations thereof.

In FIG. 3A a first far field unpinning shock 40 is applied between the electrode located in the right atrial appendage (b) and the device (a). In FIG. 3B a second far field unpinning shock 42 is applied between the electrode located distal in the coronary sinus (e) and the electrode located in the superior venae cavae (c). In FIG. 3C a third far field unpinning shock 44 is applied between the device (a) and the electrode located proximal in the coronary sinus (d).

In one embodiment, the averaged atrial DFT level is at 40 V (~0.1 J) among three selected vectors (SVC to CS, CS to LAA, RAA to LAA). With waveform optimization and electrode orientation, low voltage shocks can be further decreased below 0.1 J to ensure that the new modality remains pain-free.

Further, the novel enhanced atrial defibrillation system of the present invention can deliver optimally-shaped, low-voltage multiple pulse and sub-pulse waveforms as well as standard single biphasic waveform shock therapy. Specifically, circuitry and algorithms of the present invention may deliver a traditional waveform, as well as novel multiple sub-pulse controllable waveforms. Some embodiments of the present invention provide biphasic voltages between +/−200 V and frequencies up to 500 kHz with proper functioning over a range of capacitive loads representative of typical heart/lead interfaces. In one embodiment, the applied frequencies range from 100 kHz to 200 kHz in another the frequency ranges up to, and in some cases above, 500 khz.

Known implantable cardioverter defibrillators (ICDs) utilize a biphasic truncated exponential (BTE) waveform to deliver a shock to a patient. The waveform is generated by charging a storage capacitor to the desired voltage and closing a switch to discharge the capacitor across the patient's electrodes. While earliest ICDs generated a monophasic waveform, current devices create a biphasic waveform by which the electrode polarity is usually changed when the capacitor voltage is approximately ½ to ⅓ of the initial voltage. Biphasic waveforms have been shown to significantly decrease the energy required to defibrillate. The major reason for using BTE waveforms is the simplicity with which a large amount of energy can be transferred from a battery to the heart; meaning it can be generated in a device reasonably sized for implantation in the body. In other words, the waveform was dictated by the circuitry for generating the waveform.

However, the BTE waveform is not optimal for defibrillation from a physiological view. For many years, the top priority of optimizing shock waveform in ventricular ICDs was to reduce pulse generator size. More recently, rectangular, low-tilt truncated ascending ramp waveforms have been tested to defibrillate with lower current and energy than high-tilt capacitor-discharge waveforms. Early modeling work on the optimal pacing algorithm by Klafter, "An Optimally Energized Cardiac pacemaker", IEEE Trans Biomed Eng., 1973, Vol. 20, pp. 350-356, predicted that a slowly rising waveform would have the lowest energy requirement for stimulation. In nature, cell membranes are not capable of instantaneously changing voltage.

When a square pulse input is used to excite a cell, the membrane passively charges up towards its depolarization threshold, at which time an active ion channel opens. The fact that the transmembrane voltage rises slowly inspires the use of a slow rising waveform for defibrillation in order to reduce threshold and increase energy efficiency. As will be discussed further below, embodiments of the present invention generate such slow-rising waveforms, along with other waveform shapes ideally suited to defibrillate with minimum energy.

Several animal studies within the last decade have provided evidence that a ramp waveform may require lower defibrillation energy than the conventional biphasic truncated exponential waveform. Prior to development of custom research defibrillators, BTE was the only waveform that was practical for use in an implantable device. Damped sinusoidal waveforms had been used for several decades in transthoracic defibrillators, but the inductor used in the circuitry that produced the damped sinusoid was too large for a reasonably-sized implantable defibrillator. Although constant-current pulses, such as square waves or rectangular waves, are the most effective for defibrillation, a constant current waveform has proven to be cost and size prohibitive for implantable devices.

Despite impractical size requirements, other non-traditional waveforms have been tested using large amplifier circuits to explore delivered energy requirements for defibrillation in animals. Tests for the feasibility and safety of ascending-ramp defibrillation waveforms in humans using external research boxes have been conducted. Such testing includes a multicenter, prospective, randomized study in which these external research defibrillators were used with 63 patients. Specifically, Shorofsky et al. compared the efficacy of two ascending waveforms with a subsequent standard BTE waveform for ventricular defibrillation in patients undergoing ICD placement. The results demonstrated, for the first time clinically, that an ascending-ramp waveform defibrillates with lower energy than an optimized BTE waveform. Waveforms with a 7 ms ascending ramp decreased delivered energy at DFT by 18% and peak voltage at DFT by 24%, using a standard dual coil lead and active pectoral can system "TRIAD vector". However, creation of an ascending ramp waveform still required a bulky inductor in the capacitive discharge circuit.

Additional studies relating to non-traditional waveforms are discussed in the following articles: Kostov, et al., "Comparison Between Two Defibrillation Waveforms", Journal of Medical Engineering & Technology, November 2010, Vol 34, Nos. 7-8, pp. 429-436; Krasteva, et al., "Transthoracic Defibrillation with Chopping-Modulated Biphasic Waveforms", Journal of Medical Engineering & Technology, Vol. 25, Number 4, July/August 2001, pp. 163-168; and Antropov, et al., "An Experimental Defibrillator with Programmable Pulse Shape", Biomedical Engineering, Vol. 41, No. 1, November 2007, pp. 7-11.

The novel multi-sub-pulse controllable waveform with improved circuitry of the present invention decreases DFT further in atrial defibrillation. As noted earlier, shock pain is a concern, especially for AF patients, and it is more closely related to peak voltage than energy. An ascending-ramp waveform, for example, decreases peak voltage by about 34% as compared to a traditional waveform. Other waveforms may offer even greater reductions.

The present invention includes IACs that generate new waveforms using a more compact configuration feasible for implantation. In one embodiment, a new technique of Variable Pulse Width Modulation (VPWM) is employed to create a defibrillation pulse of alternative shape waveforms, including in the shape of an increasing ramp. In an embodiment, the control of the VPWM will be based on a real-time comparison of the actual therapy pulse to an ideal pulse shape.

In an embodiment, the voltage for creating the pulse will be provided by a high-voltage source. The capacitance of the heart in part may provide the delivery characteristics on which the pulse will be generated. Feedback from the comparison will modulate the pulse width (VPWM) to achieve the desired shape of the pulse. By utilizing this approach, the present invention dispenses with the bulky inductor that would not be feasible or cost-effective in implantable devices.

The size and energy lost in an inductor are prohibitive in utilizing one in the creation of an increasing ramp. Another issue is that once an electrical current is established in an inductor it cannot be instantaneously stopped, as can a voltage from a capacitor. The typical way of handling this residual current in an inductor is to add a clamping diode which carries the residual current once the therapy is ended. This unfortunately causes additional energy loss as the inductor current dissipates in the diode to safe levels. Energy loss such as this is a definite disadvantage in a device which is designed for very small size and long life.

An additional approach to reducing DFT uses higher than normal stimulation frequencies. Sweeney, et al. investigated the use of a somewhat high-frequency series of monophasic rectangular pulses to defibrillate the heart, as described in the article "Defibrillation Using a High-Frequency Series of Monophasic Rectangular Pulses: Observations and Model Predictions", J Cardiovasc Electrophysiology, 1996, vol. 7, pp. 134-143. Sweeney, et al. carried out their research up to 20 kHz and found that the peak current required was about double that of a continuous pulse.

While the defibrillation therapy disclosed by Sweeney was shown to be effective in reducing the energy required, it has not been implemented in a commercialized implantable pulse generator (IPG). In part this is because the ON and OFF times were too long and the membrane voltage declined to zero during the OFF phase. This prevented the buildup of a more effective pulse waveform that would require less voltage.

Conversely, embodiments of the present invention provide even higher frequency sub-pulses with shorter OFF times that permit gradual voltage buildup even with lower initial defibrillation voltage.

These higher frequency sub-pulses generated by the present invention not only achieve a lower initial defibrillation voltage, which by itself reduces perceived pain, but the high frequency nature of the sub-pulses may also lower perceived pain by taking advantage of the human body's natural electrical-filtering characteristics.

High-frequency chopping or modulation also aids in easing pain. Generally, as therapy shock waveforms propagate outside the heart, the musculo-skeletal nervous system perceives pain. However, the musculo-skeletal nervous system may act as a sort of low pass filter, such that high frequency stimulation is not readily detected, thereby reducing the perception of pain associated with high-frequency stimulation therapy. Further, because such high-frequency therapy is registered by the body differently, muscle twitch caused by heart stimulation therapy may be decreased or avoided.

Generally, embodiments of the present invention do not require a large inductor and rely mainly on additional sample and control circuits to generate custom pulse shapes. These circuits can be easily integrated into hybrid and/or integrated circuits.

Regarding safety concern of the patient, the above mentioned Sweeney paper tested frequencies between 1 and 20 kHz with no adverse effects on study participants. In addition, EN45502-2-2, which is an ICD standard from the European Union, states that certain frequencies below 1 MHz pose potential fibrillation concern. The standard goes on to state that the most problematic frequencies are between 10 and 200 Hz with a reduction in the effect of 1.5 times at 1 kHz. The effect falls off rapidly at frequencies above that. So moving to an even higher sub-pulse frequency may have the benefit of taking advantage of charge storage of cardiac tissue and will move even farther from frequencies of potential fibrillation concern.

Figure 4:
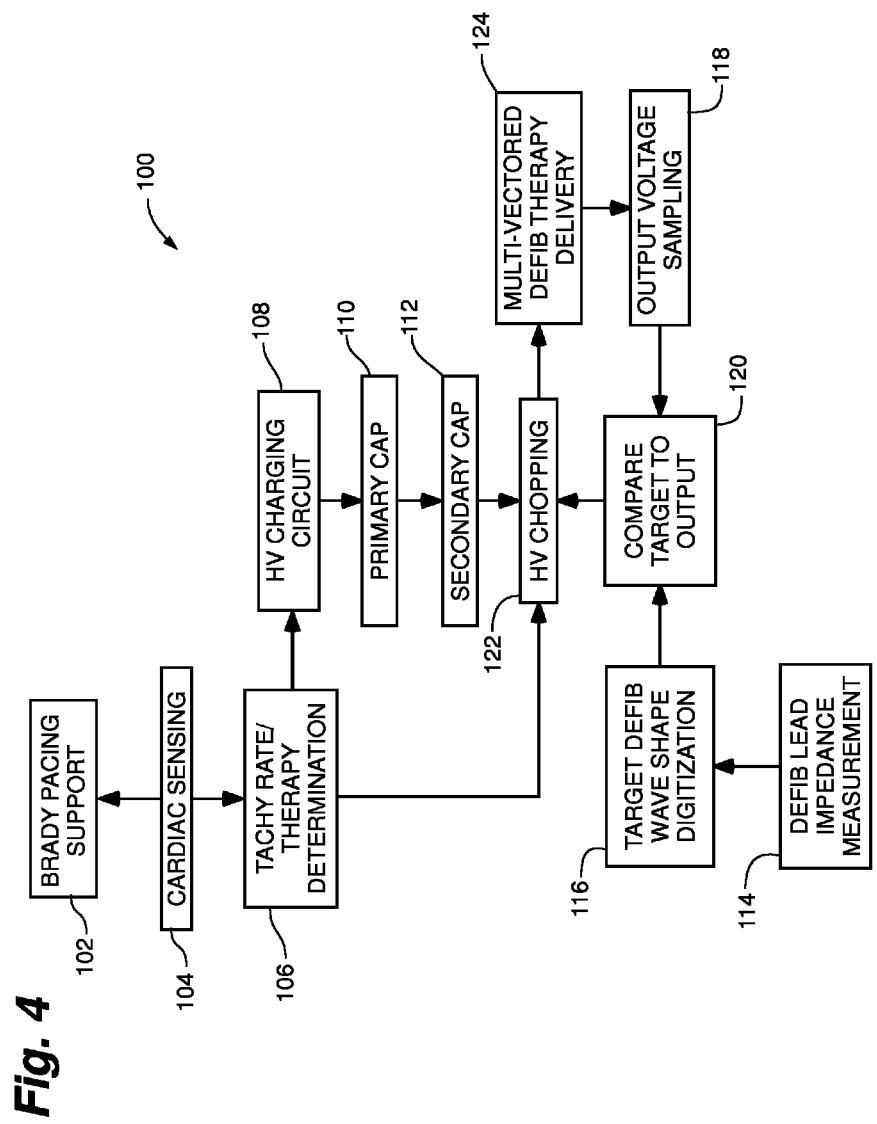
FIG. 4 is a block diagram of an embodiment of a system of the present invention.

Referring to FIG. 4, a functional block diagram of an embodiment of an AF defibrillation system 100 of the present invention is depicted. Depicted system 100 includes the following functional blocks comprising electronic circuits and electronic components: brady pacing support 102; cardiac sensing 104; tachy rate/therapy determination 106; high-voltage (HV) charging circuit 108; primary storage capacitor 110; secondary delivery capacitor 112; defib lead impedance measurement 114; target defibrillation wave-shape digitization 116; output voltage sampling 118, comparison of target to output 120, high-voltage chopping 122, and multi-vectored defibrillation therapy delivery 124.

As will be understood by those skilled-in-the-art, brady pacing support 102 provides bradycardia pacing capability, while cardiac sensing 104 monitors and senses cardiac activity. Tachy rate/therapy determination 106 detects a tachycardia rate and determines appropriate pacing therapy.

As will be discussed further below in greater detail, HV charging circuit 108 may comprise a variety of electrical circuits for charging primary storage capacitor 110. In an embodiment, HV charging circuit 108 may comprise a relatively low-voltage trickle-charge circuit with or without boost capability for slow charging of primary capacitor 110, a conventional HV charging circuit having a high-current capability battery and boost circuit, or other known HV charging circuitry.

Primary storage capacitor 110 may be any of a variety of relatively high-voltage capacitors storing energy for charging secondary delivery capacitor 112. The capacitive values of primary storage capacitor 110 depend on a number of factors including total energy required to complete the expected therapy, type of therapy, desired voltage amplitude of the therapy, speed of charging secondary capacitor 112, and other such factors as will be described further below.

Secondary delivery capacitor 112, may also comprise any of a variety of known capacitors. Secondary delivery capacitor 112 will generally be capable of storing less energy than primary storage capacitor 110.

It will be understood that while both primary storage capacitor 110 and secondary delivery capacitor 112 are referred to, and generally described as, singular components, it will be understood that either capacitor 110 or 112, or both, may actually comprise multiple capacitors, such that "capacitor" refers to one or more capacitors with an overall effective capacitance that may be achieved by parallel or serial combinations of capacitors.

Defibrillation lead impedance measurement block or circuit 114, as will be understood by those skilled in the art, includes circuits and electronic components for measuring the impedance of the leads providing the therapy to the patient.

Target defibrillation pulse (TDP) wave shape digitization circuit 116 generates a low voltage replica of the desired therapy pulse. This is digitized and stored in memory to allow comparison to the actual pulse during therapy delivery. Note that in some embodiments, this circuit will generate the target voltage as well as a minimum level for droop during the off phase of the wave-shaping process.

Output voltage pulse (OVP) sampling circuit 118 scales the OVP as it is delivered to the heart to a level safe for the comparison circuitry.

Compare target to output circuit 120 provides a comparison of the sampled OVP to the ideal TDP to determine when and how long the high voltage supply should be connected to the heart to generate the correct shape. Results are sent to the HV chopping circuit to control application of the high voltage.

HV chopping circuit 122 takes the control signal from the comparison circuit 120 and switches the high voltage either on or off, creating the appropriate voltage across the capacitance of the heart/lead interface.

Multi-vectored defibrillation therapy delivery circuit 124 provides the application of the therapy signal across any number of pairs of defibrillation electrodes.

System 100 represents a major change in how defibrillation therapy is delivered. Traditionally a charged capacitor is connected to the heart and the decay rate is set by the characteristics of the heart. This new system takes control of that therapy shape and drives it to characteristics which have been shown to be more effective at defibrillation at lower energies and in the case of atrial systems, may allow energies below pain threshold to be utilized.

In operation, cardiac-sensing circuit 104 senses and monitors cardiac signals; brady pacing support 104 provides pacing therapy as needed, while tachyrhythmia/therapy determination circuit 106 determines what therapy need be provided based on cardiac sensing circuit 104.

HV charging circuit 108 charges primary storage capacitor 110 to a predetermined voltage and energy level. Primary storage capacitor 110 charges secondary delivery capacitor 112 in preparation for therapy delivery.

Target defibrillation wave-shape digitization 116 receives lead impedance information from defibrillation lead impedance measurement circuit 114, and outputs a target wave shape to comparison circuit 120.

Comparison circuit 120 receives an output voltage sample from output voltage sampling circuit 118 and compares it to the target output voltage.

HV chopping circuit 122 "chops" the output of secondary delivery capacitor 112 such that delivery capacitor 112 is discharged in an on and off manner, creating a series of sub-pulses which comprise the waveforms delivered via multi-vectored defibrillation therapy circuit 124.

Specific embodiments of system 100 which depict and describe system 100 in greater detail will be discussed further below with respect to FIGS. 5-13.

With respect to calculations of stored energy required to meet increasing pulse requirements, calculating the required peak voltage on primary storage capacitor 110 requires an estimate of the energy to be delivered to the heart for therapy as well as the energy that needs to be delivered to the output to increase the voltage delivered to the electrodes during therapy, creating an increasing ramp.

In some embodiments, there may be multiple methods of delivering the energy to the heart. A first includes the use of both high-voltage capacitors 110 and 112. The primary storage capacitor 110 generally stores most of the energy for the therapy, and may be charged to a higher voltage than delivery capacitor 112. Delivery capacitor 112 is charged to the voltage of the leading edge of the therapy pulse. Primary capacitor 110 supplies the energy to be added to secondary capacitor 112 through a version of PWM control that includes control of the charged voltage of the secondary capacitor during delivery of therapy in order to increase the voltage on secondary delivery capacitor 112.

The delivery of sufficient electrical energy to defibrillate a heart requires an energy source which is high power and low impedance. For an implantable device it also needs to be small. Batteries are much better suited to deliver low or medium levels over longer periods of time. The capacitor is well suited to quick delivery of high levels of energy, but they suffer from a limited supply of energy. The supplied energy droops as energy is removed. So for those therapies requiring an increasing ramp waveform, a high-power source of energy, such as the one provided by primary storage capacitor 110, that is larger in voltage than the tail end of the therapy pulse or sub-pulse delivered by delivery capacitor 110, may be required.

As a result, in an embodiment there will be two capacitive elements in the output stage of this device, both will droop over time as energy is delivered to the heart for therapy. System 100 functions to deliver energy from the primary cap to the secondary cap at a rate higher than the heart pulls energy from the secondary cap. For the case of ascending-ramp waveforms, this will result in the voltage on the delivery capacitor 112 increasing over the duration of the therapy pulse width.

The overhead voltage, i.e., the value that primary storage capacitor 110 needs to be charged to in order to increase the voltage on the secondary cap, and in some cases deliver therapy directly, can be calculated based on the energy to be delivered and the energy to increase the voltage.

This embodiment of system 100 and additional embodiments are discussed below with respect to FIGS. 5-13.

With respect to sequential multiple-pulse therapy testing, in test results, a significant reduction in the AF defibrillation threshold was achieved when multiple (2-3) pulses were coupled at ~90% of AF CL. These findings were extended to an in vivo canine vagally-mediated AF model which delivered sequential multiple pulse shock therapy with far field entrainment and ATP to reduce DFT. Briefly, in normal mongrel dogs (n=12), a medial sternotomy was performed. Two disk electrodes with a diameter of 1" were placed on the right and left atrial appendages, respectively. AF was induced by rapid atrial pacing in the presence of stimulating bilateral vagus nerve at frequency of 4~20 Hz. AF that lasted for >15 min was defined as sustained. 1 to 4 monophasic (MP, 10 ms) or biphasic (BP, 6/4 ms) shocks were applied from the disk electrodes, followed with or without ATP applied from an atrial epi-pacing electrode. All shocks are triggered by R-wave and applied within 80~100 ms to avoid VF induction. Three vectors (RAA to LAA, SVC to CSd and CSp to LAA) were examined.

Results include the following: Sustained AF was mainly with dominant frequency of 11.0±1.7 Hz using vagal stimulation at 12.0±4.4 Hz. For AF (95% cases), DFT of 1BP was lower than that of 1 MP (0.73±0.43 vs. 1.68±0.98 J, p=0.008). DFT of 2BP was lower than that of 2 MP (0.37±0.14 vs. 0.93±0.59 J, p=0.01). DFT of 2BP was lower than that of 1BP (0.37±0.14 vs. 0.73±0.43 J, p=0.04). There were no significant differences among DFTs of 2BP, 3BP, and 4BP (0.53±0.41 vs. 0.39±0.36 J, ns). Atria flutter (5% cases, which had dominant frequency of 7.7±0.4 Hz) could easily be converted by multiple shocks at 0.0003±0.0001 J or ATP alone. Most importantly, sequential multiple pulse therapy could correct AF with an averaged DFT at 0.1 J, as compared with conventional biphasic shock alone (0.37 J) and biphasic shock plus ATP treatment (0.26 J) among the three vectors (n=6, P=0.008). Using the new algorithm, the successful voltage level is limited at 40V. In summary, atrial DFT could be significantly reduced by multiple pulse waveform shocks. The voltage is significantly lower than current voltage level of atrial defibrillation. The in vitro and in vivo results are encouraging for further decrease in the energy level required for cardioversion.

Referring again to FIGS. 1-3, a number of defibrillation lead systems are provided by the present invention, including: (a) SVC to RAA lead; (b) Left pulmonary artery lead (intended for experimental use to act as the active "can" of the implanted pacemaker); (c) CS lead to great cardiac vein lead. In some embodiments, lead systems will be transvenous and may include P/S electrodes. Either RAA or CS coil may be used as the anode for monophasic shocks and for the first phase of biphasic shocks. DFT may be measured using the binary search protocol (Wyse D) for monophasic 10 ms and biphasic (6+4 ms, 2:1 energy ratio between phases) shocks. In an embodiment, first shock energies are decreased following successful episodes and increased following unsuccessful episodes. Rather than starting at a relatively high energy where defibrillation will almost always be successful, the initial energy for one embodiment is near the median DFT. The binary search algorithm is rapidly gaining acceptance as the standard approach, particularly for research purposes, because of the predictable number of shocks (i.e. 3) to measure a DFT. Of note, the DFT is defined as the minimal energy to convert AF to SR.

In an embodiment, following detection of AF, either single or multiple pulse low voltage defibrillation algorithms and methods may be used. Either a single shock pulse comprised of multiple high-frequency sub-pulses will be applied throughout various phases of AF or multiple (2-5) shock pulses may be applied within one AF cycle length. In conjunction with the low voltage shock therapy, anti-tachycardia pacing (ATP, 8 pulses, 50-100% of AF CL) may be applied from the right atrial appendage.

The following is a general approach for one embodiment: 1) Measure conventional DFT for AF/AFL (>20 min) with binary protocol for biphasic (4+3 ms, 2:1 energy ratio between phases) shocks: a) Determine the excitation threshold, and pattern of excitation by far-field and local-field stimulation as a function of shock strength; b) Assess the interaction of waveforms produced by ATP and those of anchored reentry, and vary ATP cycle length by 50-100% of that of arrhythmia; c) Determine the conventional DFT and threshold for destabilization leading re-entry circuit(s) by low energy shock; and d) Optimize the destabilization of AF mother rotors or conversion of AF to AFL by varying the low-energy shock waveforms and shocking vector orientations such as using adjacent vectors and rotational field.

Such therapy may be implemented by methods, devices, and systems of the present invention as further depicted in FIGS. 5-13.

Figure 5:
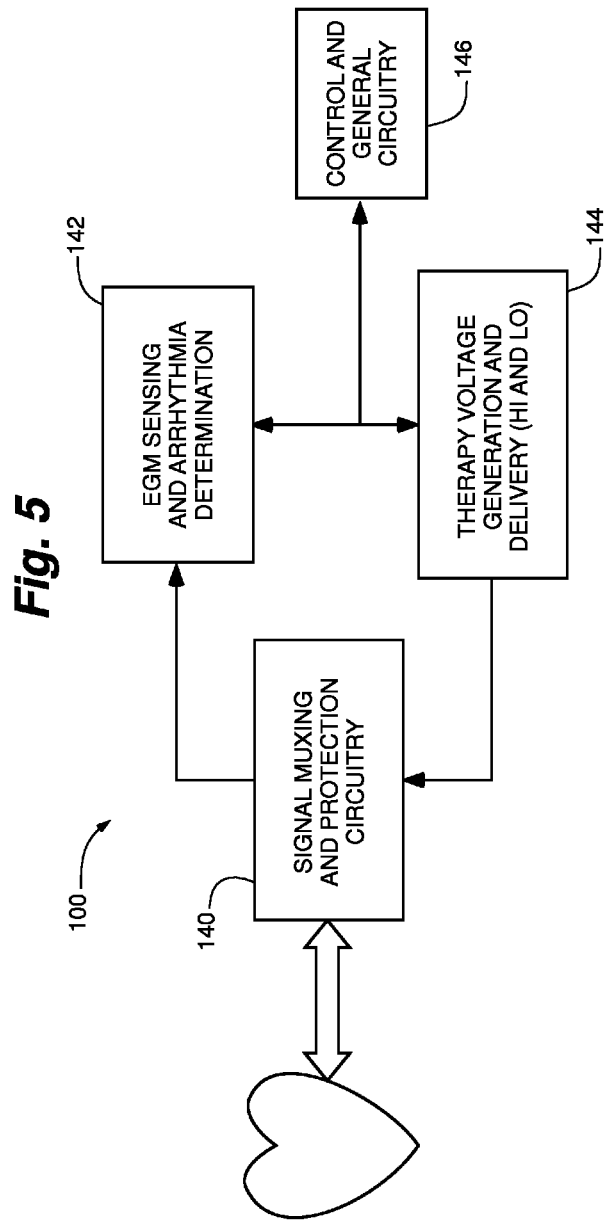
FIG. 5 is a block diagram of another embodiment of a system of the present invention.

Referring to FIG. 5, a high-level block diagram of an embodiment of system 100 of the present invention is depicted. System 100 as depicted includes signal muxing and protection therapy subsystem 140, EGM sensing and arrhythmia determination subsystem 142, therapy voltage generation and delivery subsystem 144, and control and general circuitry 146. It will also be understood that any number of known EGM sensing and/or arrhythmia determination or detection systems, including external systems or diagnostics, may be used in conjunction with the other subsystems identified in system 100, such that subsystem 142 is not limited to the specific embodiment depicted and described.

Figure 6:
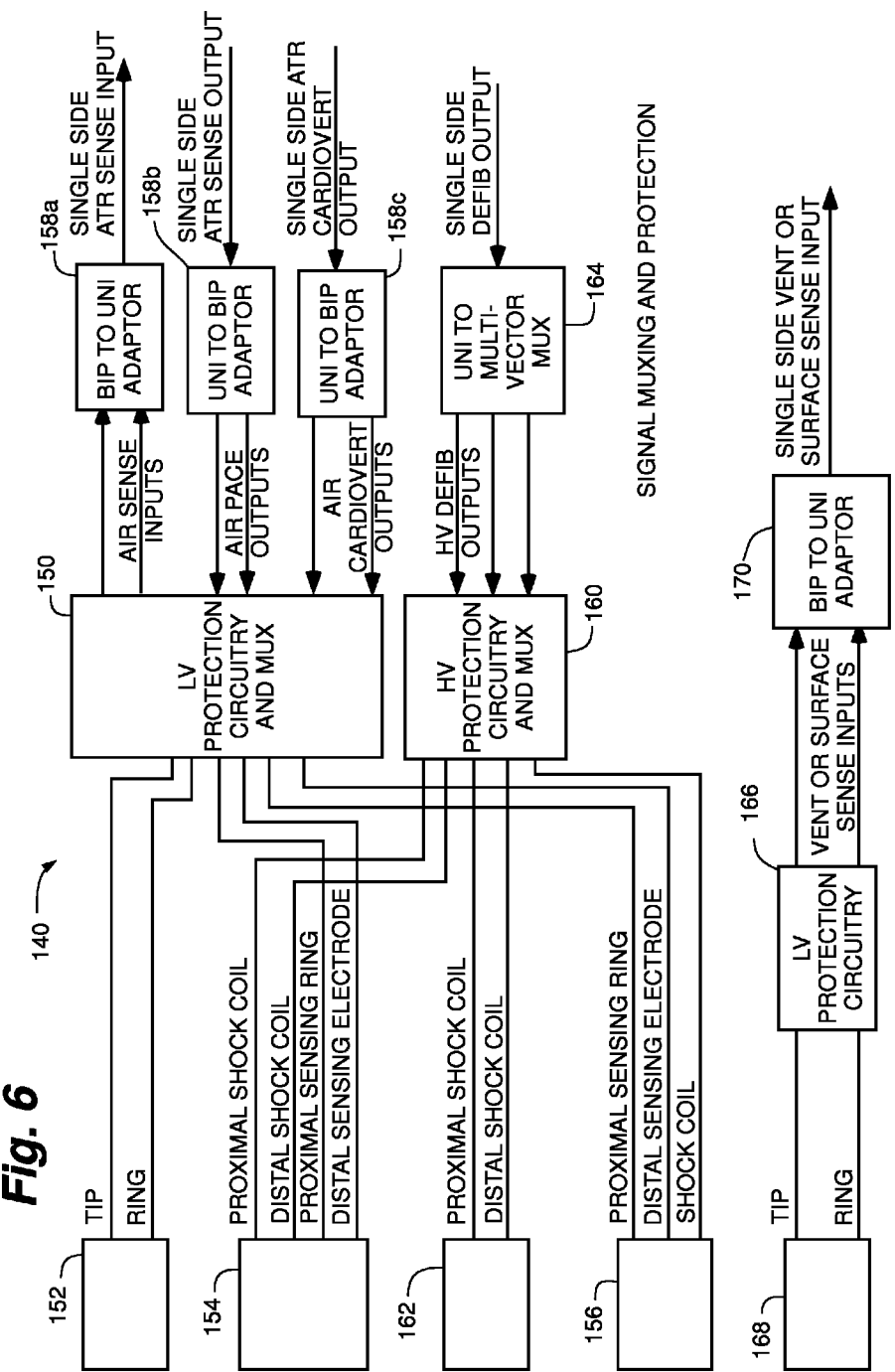
FIG. 6 is a block diagram of an embodiment of a signal multiplexing and protection circuitry of the system of FIG. 5.

Referring to FIG. 6, an embodiment of signal muxing and protection subsystem 140 of FIG. 5 is depicted. Subsystem 140 includes low-voltage (LV) protection circuitry with multiplexor (MUX) circuit 150. LV circuit 150 is in electrical communication with a number of leads, including the tip and ring portions of lead/sensor 152, and the proximal sensing rings and distal sensing electrodes of lead 154 and lead 156. LV circuit 150 receives a number of inputs from leads 152 to 156, as well as therapy voltage generation and delivery circuit 144. LV circuit 150 via its multiplexor, outputs various cardioversion and pacing signals received from circuit 144 to leads 152 to 156.

In the embodiment depicted, LV circuit 150 outputs sensed atrial inputs from leads 152 to 154 to bipolar-(BIP)-to-unipolar (UNI) adapter 158a, which in turn outputs single-side atrial sense data to EGM sensing and arrhythmia determination circuit 142.

LV circuit receives single-side atrial sense output from therapy circuit 144 via adapters 158b and 158c. In an embodiment, LV circuit 150 receives atrial pace output signals and atrial cardoversion outputs from therapy circuit 144, delivering them to the patient through leads 152 to 156.

HV protection circuitry with multiplexor circuit 160 is in electrical communication with leads 154, 162, and 156, and therapy circuit 144 via unipolar-to-multi-vector MUX 164. HV circuit 160 receives HV defibrillation pulses and sub-pulse from therapy circuit 144, delivering the therapy to the patient via leads 154, 162, and 156. The multiplexers enable the use of multi-vector, virtual-electrode polarization therapy delivery.

In addition to atrial sensing and therapy circuitry, signal multiplexing and protection circuitry subsystem 140 may also include ventricular-sensing circuitry. LV protection circuitry 166 as depicted is in electrical communication with lead 168, and outputs sensed ventricular data to EGM sensing and arrhythmia determination circuit 142 through adaptor 170. In other embodiments, subsystem 140 may also receive ventricular therapy signals from therapy circuit 144 to treat ventricular fibrillation as needed.

Figure 7:
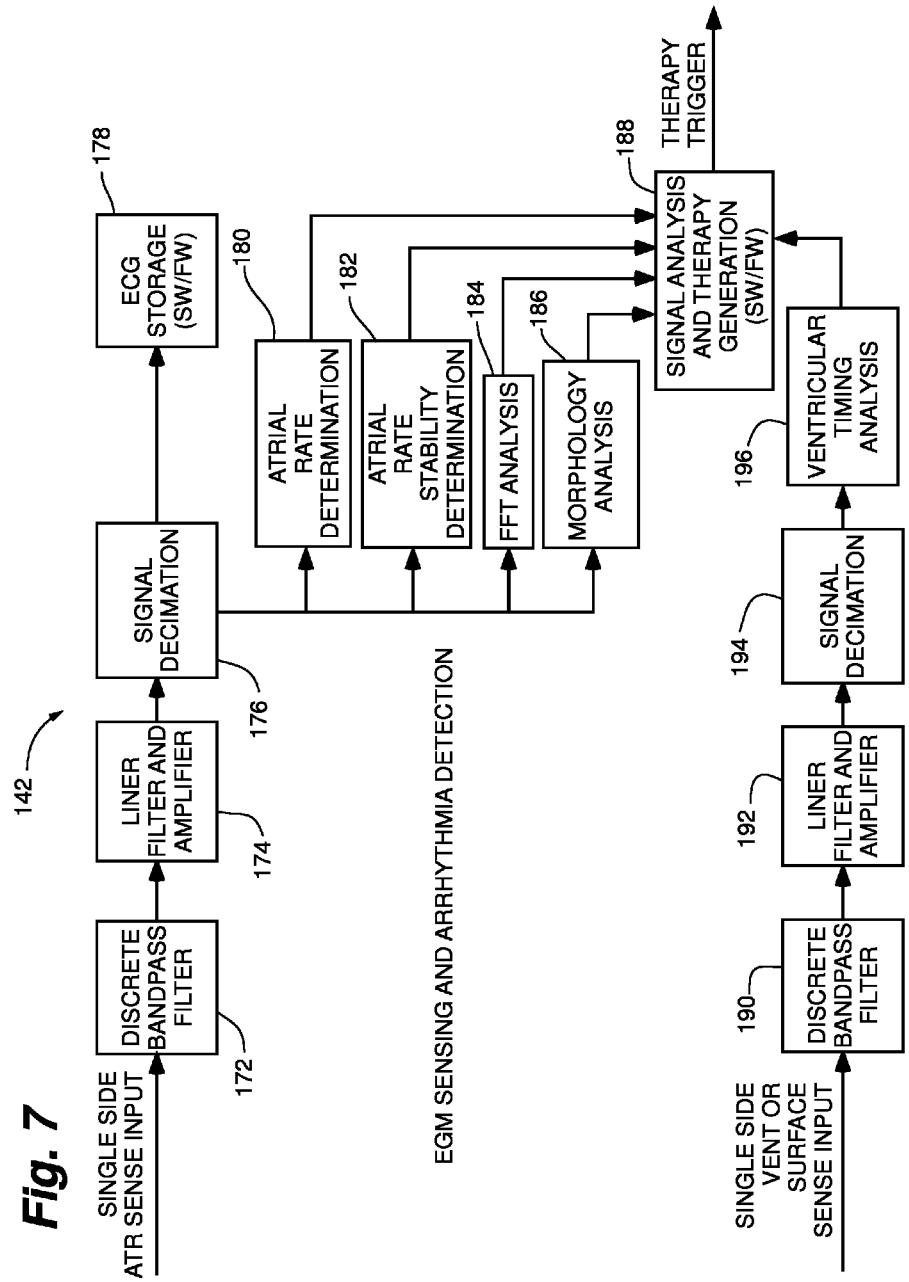
FIG. 7 is a block diagram of an embodiment of an EGM sensing and arrhythmia detection subsystem of the system of FIG. 5.

Referring also to FIG. 7, an embodiment of EGM sensing and arrhythmia detection subsystem 142 of FIG. 5 is depicted. In the depicted embodiment, EGM sensing and arrhythmia detection circuit or subsystem 142 includes atrial and ventricular sensing.

Sensed atrial input from circuit 140 is received at discrete bandpass filter 172; the filter output is further conditioned by linear filter and amplifier 174, then sent to signal decimation circuit 176. The signal is saved by EGM storage circuit 178 which may include various types of known memory devices, including volatile and non-volatile memory devices.

As will be understood by those skilled-in the-art, the conditioned atrial sense input is then analyzed by several circuits, which may include one or more processors, for eventual therapy analysis and determination. Such circuits or functions include atrial rate determination circuit 180, atrial stability determination circuit 182, fast-Fourier transform (FFT) analysis circuit 184, and morphology analysis circuit 186.

The outputs of circuits 180 to 186 are received by signal analysis and therapy generation circuit 188. In an embodiment, signal analysis and therapy generation circuit 188 also receives sensed ventricular data or signals.

Sensed ventricular input is received and conditioned by filter 190 and filter amplifier 192, and further processed by signal decimation circuit 194. Ventricular timing analysis is performed by circuit 196, such that signal and therapy generation circuit 188 receives ventricular timing data to be used for atrial therapy (and in some cases ventricular therapy).

Figure 8:
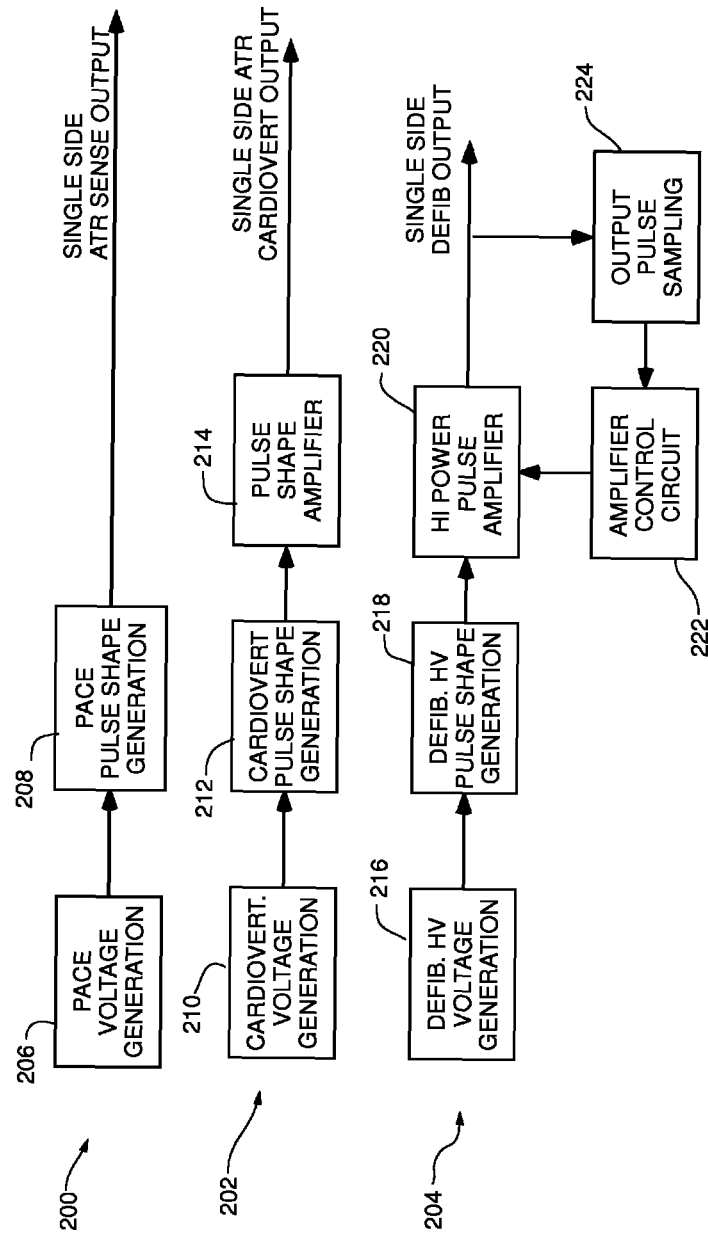
FIG. 8 is a block diagram of an embodiment of a therapy voltage generation and delivery subsystem of the system of FIG. 5.

Referring to FIG. 8, an embodiment of a therapy voltage generation and delivery subsystem 146 of the system of FIG. 5 is depicted. Therapy voltage generation and delivery circuit or subsystem 146 (therapy circuit 146) in an embodiment includes a pacing therapy portion 200, cardioversion therapy portion 202, and defibrillation therapy portion 204.

As will be understood by those skilled-in the-art, pacing therapy portion 200 includes known pace voltage generation circuit 206 and pace pulse shape generation circuit In some embodiments, rather than generating known pacing pulses, pace voltage generation and pulse shape generation circuits includes generation and pulse-shaping circuitry similar to the defibrillation pulse-shaping generation described further below. Pacing therapy is delivered to the patient via circuit 140 and the appropriate leads.

Cardioversion portion 202 includes cardioversion voltage generation circuit 210 feeding pulse-shaping circuit 212. A pulsed-shaped cardioversion waveform is amplified by pulse-shape amplifier 214. The pulsed-shaped cardioversion therapy waveform is subsequently delivered to the patient via circuit 140 and the appropriate leads.

Defibrillation portion 204, in an embodiment, includes defibrillation high-voltage generation circuit 216, defibrillation pulse-shaping generation circuit 218, high-power pulse amplifier 220, amplifier-control circuit 222 and output-pulse-sampling circuit 224.

A voltage signal output by defibrillation HV generation circuit 216 feeds pulse-shaping generation circuit 218. As described in part above with respect to FIG. 4, and as will be described further below, an output of defibrillation pulse-shaping generation circuit 222 is a series of high-frequency sub-pulses that form a shaped pulse, or waveform.

In this embodiment, the output of defibrillation generation circuit 218 is amplified by amplifier 220 and output as a therapy to circuit 140 of FIG. 5. The output therapy signal is sampled, in an embodiment, and fed through an amplifier control circuit to the pulse amplifier such that the therapy output signal can be adjusted to closely replicate a desired, predetermined defibrillation therapy.

FIGS. 9-13 depict various embodiments of atrial defibrillation pulse and sub-pulse generation and delivery circuits and systems, including embodiments of the defibrillation generation portion 204 of FIG. 8.

Figure 9:
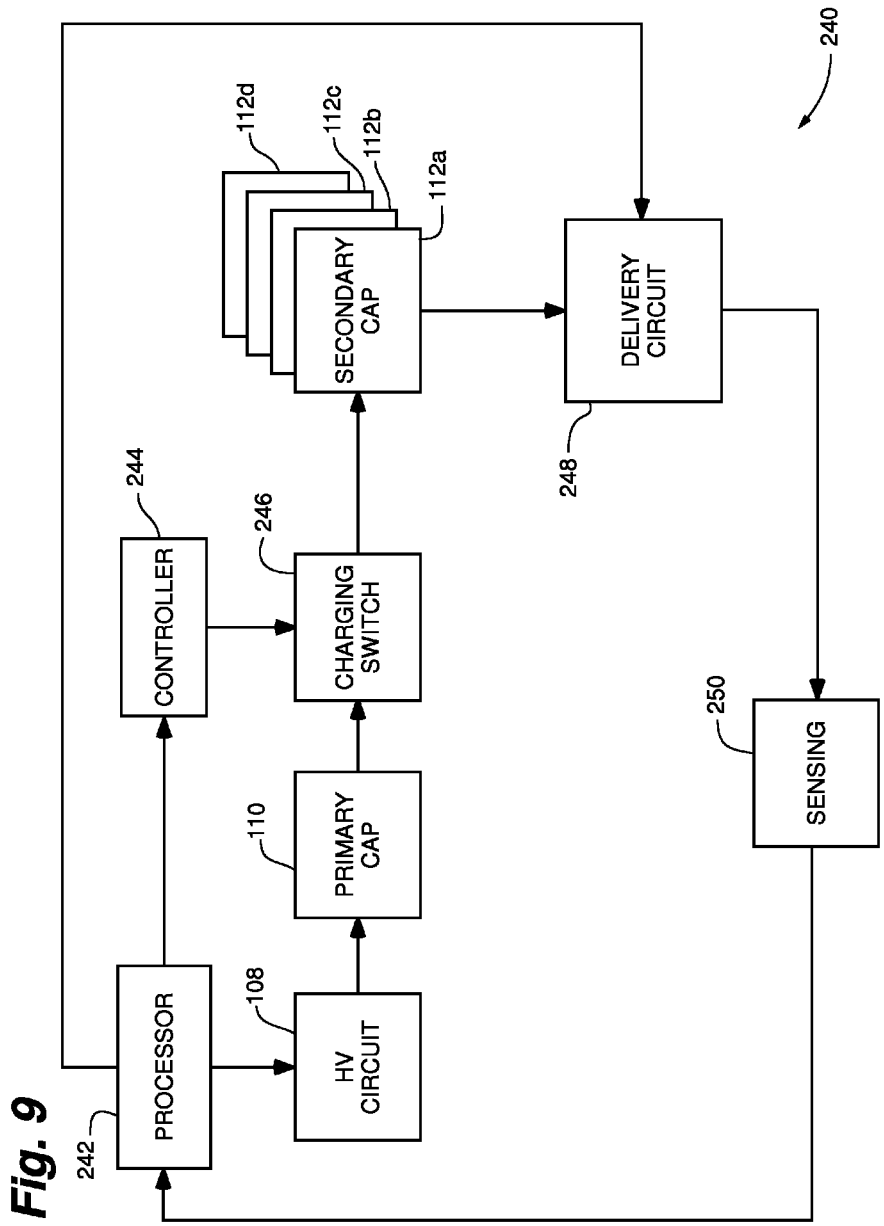
FIG. 9 is a block diagram of an embodiment of a pulse generation and delivery system of the present invention.

Referring to FIG. 9, a block diagram of a defibrillation shaped-pulse generation and delivery system 240 according to an embodiment of the present invention, is depicted.

System 240 as depicted includes processor 242, control circuit 244, charging switch 246, HV circuit 108, primary capacitor 110, secondary delivery capacitor 112, therapy delivery circuit 248 and sensing circuit 250.

Processor 242 may be a processor dedicated to the generation and delivery circuit 240, but may also be a processor managing other systems and subsystems of the devices and circuits depicted in FIGS. 5-8. It will be understood that processor 242 may comprise any of a number of known microprocessors, microcontrollers, and so on, with our without built-in memory devices. Processor 242 outputs data and control signals to control circuit 244, and in those including sensing feedback as depicted, receives sensing input from sensing circuit 250.

Control circuit 244 may include various electronic control components, including control circuits and switches, clocks, and in some embodiments, a processor. In an alternate embodiment, portions, or all of, control circuit 244 may be integrated into processor 242. Control circuit 244 controls charging switch 246, and the charging of secondary capacitors 112.

HV circuit 108, as described in embodiments above, is electrically connected to primary capacitor 110 and provides charging and boost circuitry to charge primary capacitor 110.

Primary capacitor 110 is also electrically connected to charging switch 246 which selectively connects secondary capacitors 112 to primary capacitor 110.

Delivery circuit 248 is electrically connected to secondary capacitors 112 and sensing circuit 250. An output of sensing circuit 250 is electrically connected to processor 242. In an alternate embodiment, an output of sensing circuit 250 is connected to control circuit 244. In various embodiments, therapy may or may not be delivered synchronously with some aspect of a sensed ventricular EGM. In manual mode, for example, the therapy may be initiated at a medical facility where an automated external defibrillator (AED) is present and staffed in case of emergency and the patient may be connected to an external EKG system that would be used as a trigger filter for initiating the delivery of AF therapy.

In general operation, processor 242 controls operation of HV circuit 108 which charges primary storage capacitor 110. Processor 242 also directs control circuit 244 to selectively control charging switch 246. As will be discussed further below with respect to FIG. 12, in an embodiment, processor 242 may also store, and in some circuits output, a desired or target therapy output signal for use in adjusting the delivered therapy. As depicted, processor 242 may also control aspects of delivery circuit 248. Control circuit 244 in an embodiment turns charging switch on to charge one or more secondary capacitors 112. In one embodiment, the duration that charging switch 246 is "on" such that primary storage capacitor 110 is electrically connected to, and thereby charging, secondary delivery capacitors 112 determines the voltage and energy stored in delivery capacitors 112. In other embodiments, described further below with respect to FIGS. 12 and 13, other electronic components and circuitry may be incorporated into charging switch 246 to determine a voltage amplitude of secondary delivery capacitor 112.

Delivery circuit 248 receives an output of secondary capacitors 112, applying the discharge of capacitors 112 to electrodes or leads connected to a patient's heart, thereby delivering the desired therapy. Control of the discharging of secondary capacitors 112, namely the timing and duration of applying the voltage across secondary capacitors 112 to the electrodes is generally a function of processor 242 causing delivery circuit 248 to switch secondary capacitors 112 in and out of delivery circuit 248.

Although generally directed toward relatively low-voltage, low-energy atrial defibrillation, shaped-pulse generation and delivery system 240 may in some embodiments also be capable of providing ventricular defibrillation therapy as an alternative or back-up therapy when the appropriate leads are implanted in the patient. In one embodiment, system 240 includes a relatively low-power HV circuit 108 and relatively low-energy capacitors 110 and 112 for delivery of either low-energy atrial or low-energy ventricular defibrillation therapy. In another embodiment, system 240 includes a having faster charging, high-energy HV circuit 108 combined with a high-voltage, high-energy storage capacitor 110 that may be more readily suited for delivering both low-energy atrial defibrillation therapy and high-energy ventricular defibrillation as needed.

Referring to FIGS. 10-13, embodiments of shaped-pulse generation and delivery system 240 are depicted.

Figure 10:
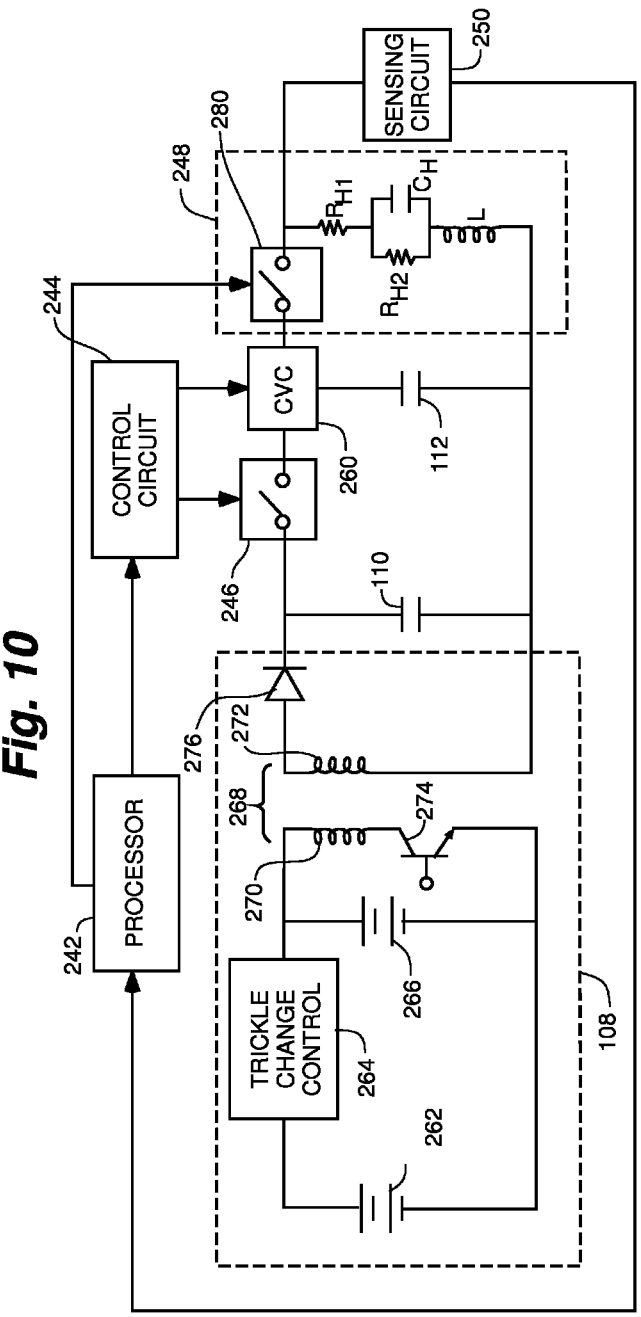
FIG. 10 is an embodiment of an exemplary circuit of the pulse generation and delivery system of FIG. 9.

Referring specifically to FIG. 10, an embodiment of shaped-pulse generation and delivery system 240 of FIG. 9 is depicted. In this embodiment, system 240 again includes processor 242, control circuit 244, charging switch 246, HV circuit 108, primary capacitor 110, secondary delivery capacitor 112, therapy delivery circuit 248 and sensing circuit 250. In this embodiment, system 240 also includes a capacitor-voltage-control (CVC) circuit 260 for determining a voltage of secondary delivery capacitor 112.

In this particular embodiment, HV circuit 108 comprises a conventional, relatively low-current charging circuit that comprises primary, non-rechargeable battery 262, trickle-charge (slow-charge) control circuit 264, rechargeable battery 266, high-voltage boost transformer 268 with primary coil 270 and secondary coil 272, transistor switch 274 and rectifying diode 276. HV circuit 108 may comprise other, known, relatively low-power HV circuits.

Delivery circuit 248 comprises therapy-delivery switching circuit 280 electrically connected to resistive elements $R_{H1}$, $R_{H2}$, capacitive element $C_H$, and inductive element L representing a patient's heart and connected electrode leads. Therapy-delivery switching circuit 280 may comprise a simple semiconductor switch, as essentially depicted, but in other embodiments, may comprise an H-bridge or other switching circuit as will be described in further detail below, and with respect to FIG. 13.

Capacitor-voltage control circuit 260 may comprise any number of circuits capable of controlling the charging voltage to secondary delivery capacitor 112. In an embodiment, CVC circuit 260 may comprise a switchable voltage divider controlled by control circuit 244 as described further below and depicted in FIG. 13.

In operation, HV circuit 108 slowly charges primary storage capacitor 110 until fully charged at t. As described briefly above with respect to FIG. 5, storage capacitor 110 generally must store enough energy to provide all of the energy required for the anticipated shock therapy as HV circuit 108 is not capable of quickly charging storage capacitor 110, nor delivering sufficient therapy energy in the very short time required.

Charging switch 246, controlled by control circuit 244 and processor 242, is selectively opened and closed to bring delivery capacitor 112 into electrical connection with storage capacitor 110, via CVC circuit 260. In an embodiment, charging switch 246 comprises a semiconductor switch, such as a transistor.

When charging switch 246 is closed, storage capacitor 110 charges secondary delivery capacitor 112. In the absence of CVC circuit 260, the voltage across delivery capacitor 112 would rise up to be equal to the voltage of storage capacitor 110. When shaped-pulse generation and delivery system 240 includes CVC circuit 260 as depicted in FIG. 10, CVC circuit 260 causes a voltage at delivery capacitor 112 to be different than the voltage at storage capacitor 110. Generally, the voltage at delivery capacitor 112 will be less than the voltage at storage capacitor 110. The voltage charge on delivery capacitor 112 in combination with the particular electrical characteristics of the heart and electrodes primarily determines the voltage of the sub-pulse delivered to the heart.

When charging switch 246 is open, storage capacitor 110 and delivery capacitor 112 are electrically disconnected, and both capacitors remain charged.

Processor 242, or in an alternative embodiment control circuit 244, selectively controls therapy-delivery switching circuit 280, such as by opening and closing a switch (monophasic) or multiple switches (biphasic), thereby causing energy stored in delivery capacitor 112 to be delivered to the heart via the electrodes, depicted as resistive elements $R_{H1}$, $R_{H2}$, capacitive element $C_H$, and inductive element L, thereby delivering the electrical shock therapy. Such selective control comprises a form of pulse-width modulation. The longer therapy-delivery switching circuit 280 is "closed"

such that delivery capacitor 112 discharges its energy to the heart, the longer the duration of the delivered energy sub-pulse. Causing switching circuit 280 to open and close at high frequencies results in multiple, short-duration sub-pulses being delivered.

In an embodiment, therapy-delivery switching circuit 280 includes one or more power MOSFETs. Known defibrillators typically rely on IGBTs to switch delivery capacitors in and out of a circuit because of their high-current carrying capacity. However, the present invention enables the use of power MOSFETS by switching them on and off at a high frequency rate, and subsequently lower duty cycle, as compared to IGBTs in a traditional non-PWM pulse generation and delivery circuit. The benefits of using multiple MOSFETs in switching circuit 280 is discussed further below with respect to FIG. 13.

Between delivery of sub-pulses, secondary delivery capacitor 112 may be charged to a predetermined voltage by primary storage capacitor 110 via charging switch 246 and CVC circuit 260. In such an embodiment, switching circuit 280 is generally "open" when charging circuit 246 is "closed", such that energy from storage capacitor 110 is transferred to delivery capacitor 112, rather to the heart and electrodes. The predetermined voltage may be different from sub-pulse to sub-pulse to create a shaped-pulse. Embodiments of various shaped-pulses, comprised of multiple, high-frequency sub-pulses are depicted and described further below with respect to FIGS. 14-19.

Sensing circuit 250 senses an electrical characteristic of the delivered therapy, such as a voltage, and outputs a control signal to processor 242. Processor 242 in an embodiment compares the feedback received from sensing circuit 250 to a predetermined waveform, and adjusts the therapy as needed. Adjustments may include sub-pulse voltage amplitude, sub-pulse duration, and so on. Storage capacitor 110 and delivery capacitor 112 may be sized to accommodate a desired therapy.

Figure 11:
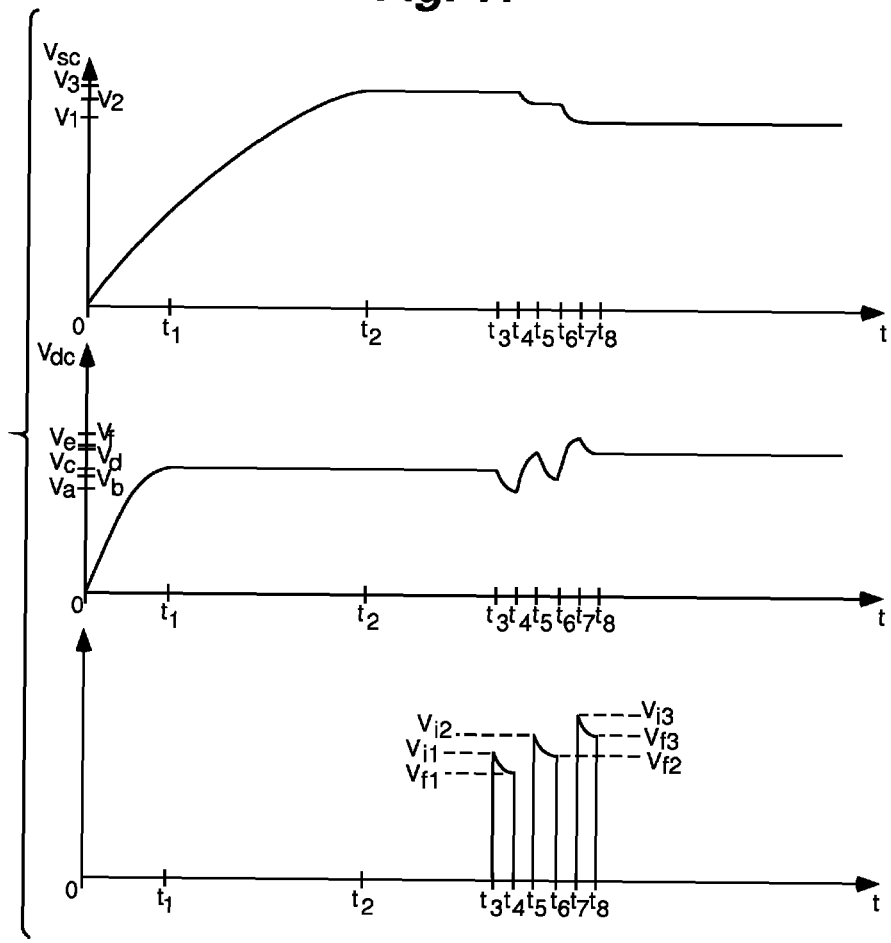
FIG. 11 is a timing diagram depicting the operation of the circuit of FIG. 10.

Referring also to FIG. 11, a timing diagram depicts the operation of system/circuit 240 as described above. FIG. 11 depicts a graph of primary storage capacitor 110 voltage, $V_{sc}$, versus time; a graph of secondary delivery capacitor 112 voltage, $V_{dc}$, versus time; and a graph of sub-pulse voltage $V_p$ as delivered to the heart and electrodes. The position (open or closed) of charging switch 246 and delivery switch 280 as a function of time are also indicated.

At time zero, $t_0$, charging switch 246 is closed and delivery switch 280 is open. HV circuit 108 charges primary storage capacitor 110 to its full potential $V_3$ over the time period of $t_0$ to $t_2$; storage capacitor 110 charges delivery capacitor to $V_c$ over the time period of $t_0$ to $t_1$.

At $t_3$, therapy is initiated. Charging switch 246 is opened, disconnecting storage capacitor 110 from delivery capacitor 112; therapy delivery switch 280 is closed, electrically connecting delivery capacitor 112 to the heart and electrodes. Storage capacitor voltage $V_{dc}$ decays from $V_b$ to $V_a$ from $t_3$ to $t_4$, creating a sub-pulse at the heart having an initial voltage $V_{i1}$ and falling to a final voltage of $V_{f1}$. As charging switch 246 is open, the voltage and stored energy of storage capacitor 110 remains unchanged.

At $t_4$, therapy delivery switch 280 is closed, and charging switch 246 is opened. Delivery capacitor 112 is charged to $V_d$ by storage capacitor 110 from $t_4$ to $t_5$; storage capacitor voltage $V_{sc}$ decays from $V_3$ to $V_2$ as energy is transferred to delivery capacitor 112. No sub-pulse is delivered to the heart.

At $t_5$, another sub-pulse is delivered: charging switch 246 is opened; therapy delivery switch 280 is closed; delivery capacitor 112 decays from $V_d$ to $V_c$ at $t_6$; a second sub-pulse having an initial voltage of $V_{i2}$ and decaying to a final voltage of $V_{f2}$ at $t_6$ is delivered to the heart. $V_{sc}$ at storage capacitor 110 remains unchanged at $V_2$.

At $t_6$, therapy delivery switch 280 is opened; charging switch 246 is closed; delivery capacitor 112 charges up to $V_f$ from $t_6$ to $t_7$; storage capacitor 110 decays to $V_1$ at $t_7$.

At $t_7$, a third sub-pulse is delivered: charging switch 246 is opened; therapy delivery switch 280 is closed; delivery capacitor 112 decays from $V_f$ to $V_e$ at $t_8$; the third sub-pulse having an initial voltage of $V_{i3}$ and decaying to a final voltage of $V_{f3}$ at $t_8$ is delivered to the heart. $V_{sc}$ at storage capacitor 110 remains unchanged at $V_1$.

With respect to storage capacitor sizing and energy storage, a capacitance value may be derived based on the total energy to be delivered with a safety margin. As described briefly above, the total therapy energy can be calculated based on a known total value, for instance, 1 J. The total energy can also be calculated by determining the energy in each sub-pulse delivered.

Peak amplitude voltage of individual sub-pulses, must also be considered. Storage capacitor 110 must be able to charge delivery capacitor 112 to the desired sub-pulse delivery voltage. The ability to charge delivery capacitor 112 to the desired peak voltage becomes should be maintained in the later portions of therapy delivery, as the voltage on storage capacitor 110 generally tends to fall as it repeatedly charges delivery capacitor 112, and as HV circuit 108 fails to keep up with energy demands (by design). In a case where a 50V sub-pulse need be delivered at an end of a cycle therapy, storage capacitor 110 should have enough energy, and voltage, to charge storage capacitor 112 to the intended therapy sub-pulse voltage.

In the case of a low-energy atrial defibrillation shock therapy delivering a total of approximately 1 Joule of energy (E), with an initial voltage charge of 100V ($V_i$) and a final voltage charge of 50V ($V_f$), a capacitance value (C), assuming lossless circuits, may be approximated using the formula $E=\frac{1}{2}C(V_i^2-V_f^2)$, such that C=267 µF. In practice, the capacitance value may be increased to ensure sufficient overall therapy energy, or to accommodate multiple instances of therapy in a short time period.

In other embodiments, a capacitance value C of storage capacitor 110 may be more closely calculated based upon expected initial and final voltages of individual sub-pulse voltages, rather than initial and final voltages at pulse, stage, or total therapy start and end times, rather than the simplified formula above.

Delivery capacitor 112 may be sized similarly, based upon a maximum expected energy delivered in a single sub-pulse as determined by both voltage and sub-pulse duration.

In the event that a low-energy ventricular defibrillation therapy is desired, capacitors 110 and 112 may be sized to be able to deliver the shaped-pulses required of a particular ventricular defibrillation therapy. Assuming that the low-energy ventricular therapy requires a somewhat higher voltage and energy as compared to the low-energy atrial therapy, capacitors 110 and 112 may be sized based upon the greater energy needs of the ventricular therapy, but may still deliver the lesser energy of the atrial therapy by control of the charging and discharging of delivery capacitor 112.

Figure 12:
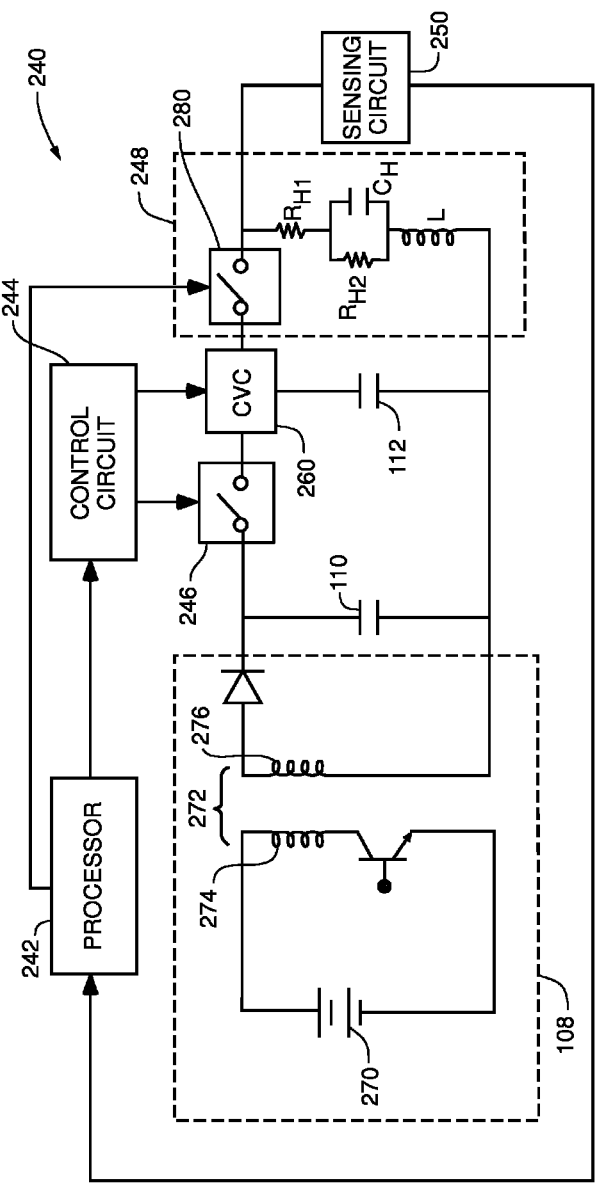
FIG. 12 is a is another embodiment of an exemplary circuit of the pulse generation and delivery system of FIG. 9.

Referring to FIG. 12, an alternate embodiment of shaped-pulse generation and delivery system 240 is depicted. Though this embodiment of system 240 is substantially similar to the embodiment depicted in FIG. 10, the embodiment depicted in FIG. 12 includes a traditional, fast-charging, relatively high-power HV circuit 108. Such an embodiment may be preferable for producing shaped-pulses for atrial therapy, but also for delivering high-energy ventricular therapy.

In the depicted embodiment, HV circuit 108 includes high-energy battery 270, high-voltage boost transformer 290 with primary coil 292 and secondary coil 294, rectifying diode 296, and transistor switch 298. HV circuit 108 may comprise other, known, relatively high-power HV circuits.

Unlike the embodiment of HV circuit 108 depicted in FIG. 10, the embodiment depicted in FIG. 12 typically delivers enough energy at an appropriately high voltage to primary storage capacitor 110 such that ventricular defibrillation therapy may be delivered following atrial defibrillation therapy. In such an embodiment, both storage capacitor 110 and delivery capacitor 112 may have capacitance values and voltage ratings that are significantly higher than those of system 240 of FIG. 10.

During atrial defibrillation therapy, delivery capacitor 112 may be charged to a lower energy for delivery of low-energy sub-pulses, as controlled by control circuit 244, charging switch 246, and capacitor voltage control circuit 260. In the event that high-energy ventricular therapy is necessary, delivery capacitor 112 can be charged to an appropriately high voltage and discharged through circuit 248 as described above.

Alternatively, storage capacitor 110 could be discharged directly across the heart. In the atrial defibrillation operation described above, charging switch 246 is closed during charging of delivery capacitor 112, which is between sub-pulses, while therapy-delivery switching circuit 280 is open. During therapy delivery, switch 246 is open, and switch 280 is closed. In an embodiment that also delivers ventricular therapy, switches 246 and 280 may both be closed during therapy delivery so as to discharge storage capacitor 110 directly to the heart, rather than through a controlled pulsing of delivery capacitor 112.

Figure 13:
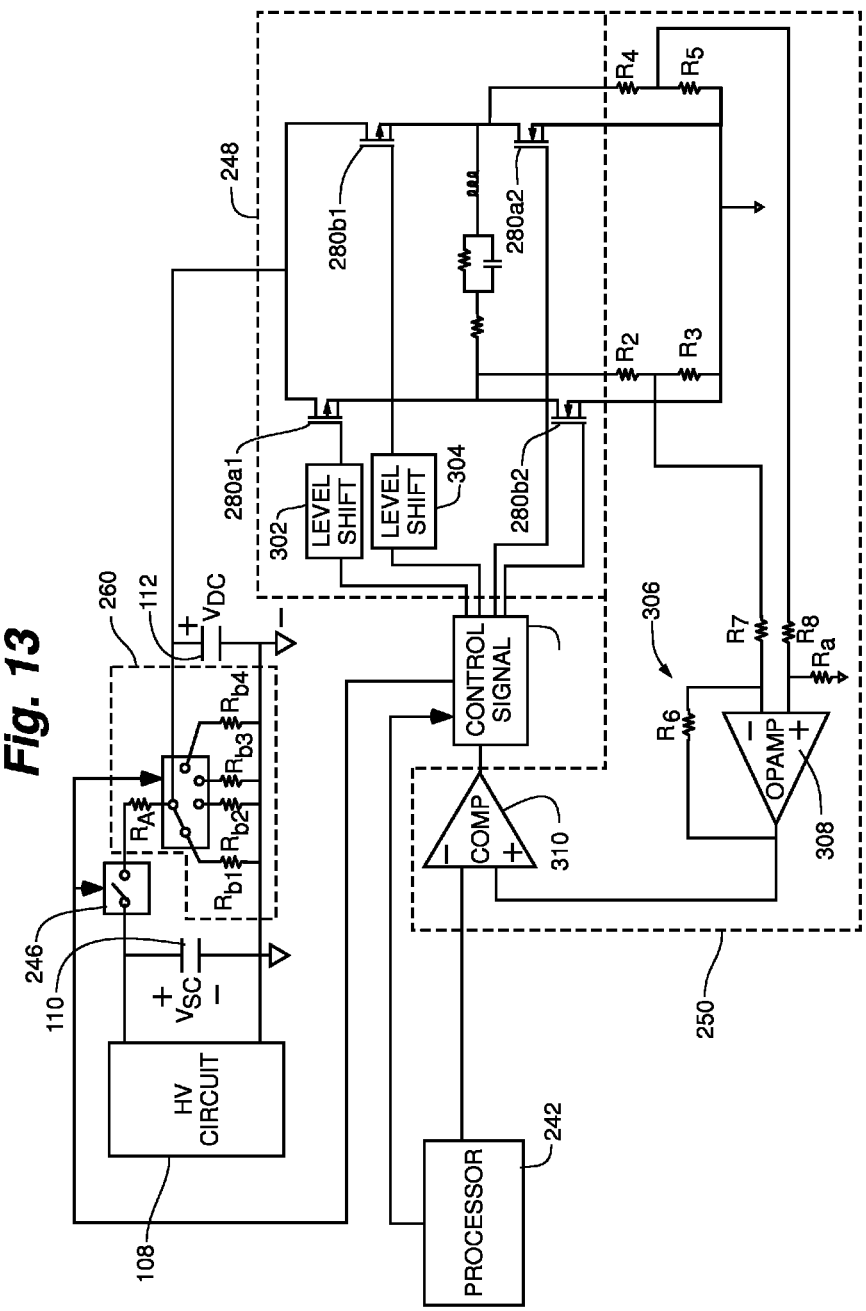
FIG. 13 is yet another embodiment of an exemplary circuit of the pulse generation and delivery system of FIG. 9.

Referring to FIG. 13, a circuit diagram of an embodiment of a shaped-pulse generation and delivery system 240 is depicted. The embodiment of delivery system 240 depicted in FIG. 13 is substantially the same as those depicted and described with respect to FIGS. 10 and 12, though the depiction of FIG. 13 depicts additional details of an embodiment of therapy delivery circuit 248 and capacitor voltage control circuit 260. The depicted pulse generator is capable of producing a variety of "arbitrary" pulse waveforms, including ascending and descending pulsed waveforms.

Shaped-pulse generation and delivery system 240 as depicted again includes processor 242, control circuit 244, charging switch 246, HV circuit 108, primary capacitor 110, secondary delivery capacitor 112, therapy delivery circuit 248, sensing circuit 250 and capacitor-voltage control circuit 260. In this embodiment, a feedback loop of sensing circuit 250 is directed into control circuit 244, rather than processor 242.

In the depicted embodiment, therapy delivery circuit 248 includes two pairs of high-voltage power MOSFETs, 280a1 and 280a2, and 280b1 and 280b2, forming an H-bridge for generation and delivery of biphasic sub-pulses across the electrodes and heart. Conversely, the embodiments described above with respect to FIGS. 10 and 12 depicted switching circuit 280 as a single switch. The electrical properties of the heart are shown by components $R_{hrt1}$, $R_{hrt2}$, $C_{hrt1}$ and $L_{ld}$. Components from this group that will be involved in the smoothing of any chopped signal are $R_{H2}$ and $C_H$, $R_{hrt2}$ and $C_{hrt1}$. Any charge stored in the heart circuitry will be stored in $C_H$ and once any delivered sub-pulse ends, the stored charge will dissipate from $C_H$ through $R_{H2}$. Therefore, in an embodiment, the time constant of $C_H*R_{H2}$ may determine the maximum OFF time of any switching or chopping circuit, or namely the time between sub-pulses.

Power MOSFETs 280 may include any variety of known high-voltage power MOSFETs, such as a HEXFET Power MOSFET, Model IRFP4768PbF, or IRF 340, as provided by International Rectifier of El Segundo, Calif. In one such embodiment, MOSFETs 280 have a voltage rating of 250V, and a drain current rating of 93 A. MOSFETs 280 may generally be selected to operate within the parameters of the desired delivered therapy, which includes operating at the charged voltage of secondary delivery capacitor 112. As will be described further below, selective control of MOSFETs 280 creates the chopped therapy waveform comprising multiple sub-pulses.

As will be understood by those skilled-in-the-art, therapy delivery circuit 248 may also include level shift circuits 302 and 304 for triggering operation of MOSFETs 280a1 and 280b1.

In this particular embodiment, capacitor voltage control circuit 260 comprises a switchable voltage divider that includes resistor $R_a$ connectable to any of $R_{b1}$, $R_{b2}$, $R_{b3}$, or $R_{b4}$. Each resistor $R_b$ generally has a different resistive value for charging secondary capacitor 112 to different voltages. Although only four resistors $R_b$ are depicted, it will be understood that any number of resistors $R_b$ could be used, depending on the number of desired voltage gradations desired.

In this embodiment, sensing circuit 250 includes; first voltage divider comprising resistors R2 and R3, and second voltage divider comprising resistors R4 and R5; amplifier circuit 306 with op amp 308 and resistors R6 to R9; and comparator 310.

Operation of shaped-pulse generation and delivery system 240 is substantially similar to that of systems 240 described above with respect to FIGS. 10 and 12.

High-voltage charging circuit 108 charges primary storage capacitor 110 to a predetermined voltage, $V_{sc}$ that is at or above the maximum sub-pulse voltage to be delivered by secondary delivery capacitor 112.

Processor 242 and/or control circuit 244 causes charging switch 246 to close, thereby causing secondary delivery capacitor 112 to be in electrical connection with primary storage capacitor 110 via switchable voltage divider 260. One of resistors $R_{b1}$ to $R_{b4}$ is selected to create the voltage divider, which determines the actual voltage at delivery capacitor 112. If $R_{b1}$ is selected as depicted, then delivery capacitor 112 charges to a voltage $V_{dc} = V_{sc} \times R_{b1}/(R_a + R_{b1})$. Increasing the resistance value of $R_{b1}$ generally causes the $V_{dc}$ to decrease. In an embodiment where $R_{b1} < R_{b2} < R_{b3} < R_{b4}$, switching from $R_{b1}$ to $R_{b2}$ to $R_{b3}$ and to $R_{b4}$ causes the deliver voltage $V_{dc}$ to decrease. The values of $R_b$ may be selected based on desired therapy voltages. Further switchable voltage divider 260 may be switched between pulses such that each sub-pulse voltage is individually controllable.

In other embodiments, charging switch 260 may comprise other circuits for determining the voltage of charged secondary delivery capacitor 112. In one such embodiment, as described briefly above, charging switch 260 may be a high-speed transistor switch, and the amount of time that switch 260 remains closed, in combination with the time constant determined by the capacitance value of secondary capacitor 112 and equivalent circuit resistance, determines the voltage amplitude of charged secondary capacitor 112.

When implantable device 100 determines that atrial defibrillation therapy should be delivered to the patient (refer back to FIGS. 4-9), control circuit 244 selectively turns one of MOSFET pair 280a1,2 and 280b1,2 on and off at high-frequency rate, followed by turning the other of the two MOS- FET pairs on and off. When either MOSFET pair conducts, secondary discharge capacitor 112 discharges, delivering a sub-pulse through the patient's heart and attached electrodes.

In an embodiment, MOSFET pair 280a1,2 delivers multiple sub-pulses to form a first portion (positive) of a biphasic pulse, followed by MOSFET pair 280b1,2 delivering multiple sub-pulses to form a second portion (negative) of a biphasic pulse. If a monophasic pulse is desired, only one pair of MOSFETs, or even a single MOSFET, may be used, as will be understood by those skilled-in-the-art.

A traditional H-bridge delivery circuit typically comprises pairs of IGBTs which are left "on" for the duration of the entire therapy pulse, which may only comprise one or several relatively high voltage, high-energy pulses. Unlike such a traditional delivery circuit, the circuit of the present invention uses a form of pulse-width modulation to rapidly turn a MOSFET pair, such as 280a1 and 280a2 on and off, thereby generating short-duration, high-frequency pulses, rather than one long continuous pulse. As described above, switching frequencies may range from 100 kHz to 200 kHz, but in some embodiments may be as high as 500 kHz, or even greater. Embodiments of such therapies of the present invention are depicted and described further below with respect to FIGS. 14-19.

In an embodiment, sensing circuit 250 continuously samples an output voltage across the heart at the first and second voltage dividers, amplifies the sampled voltage at amplifier circuit 306, and compares it to an ideal voltage waveform as supplied by processor 242. The output of comparator 310 is used by control circuit 244 to adjust a voltage output of delivery capacitor 112 by controlling operation of capacitor voltage control circuit 260 and/or adjusting the duration of delivered pulses by increasing or decreasing the time that MOSFETs 280 are conducting.

In this manner, shaped-pulse generation and delivery circuit 240 of the implantable defibrillator device 100 of the present invention delivers a pulse-width modulated, variable voltage amplitude shock therapy to a patient.

The use of IGBTs in implantable devices presents several drawbacks overcome by the present invention and the use of MOSFETs acting as PWM devices. IGBTs are typically used because of their high-power characteristics. MOSFETs were traditionally avoided because of their inability to operate at high voltage, high-current conditions without creating excess heat. However, by rapidly turning the MOSFETs on and off, rather than operating them for sustained periods of time, and by operating at therapy voltages typically lower than traditional voltages, circuits of the present invention can take advantage of the small size MOSFETs to deliver effective, pain-free therapy in a smaller package and at a lower cost.

Figure 14:
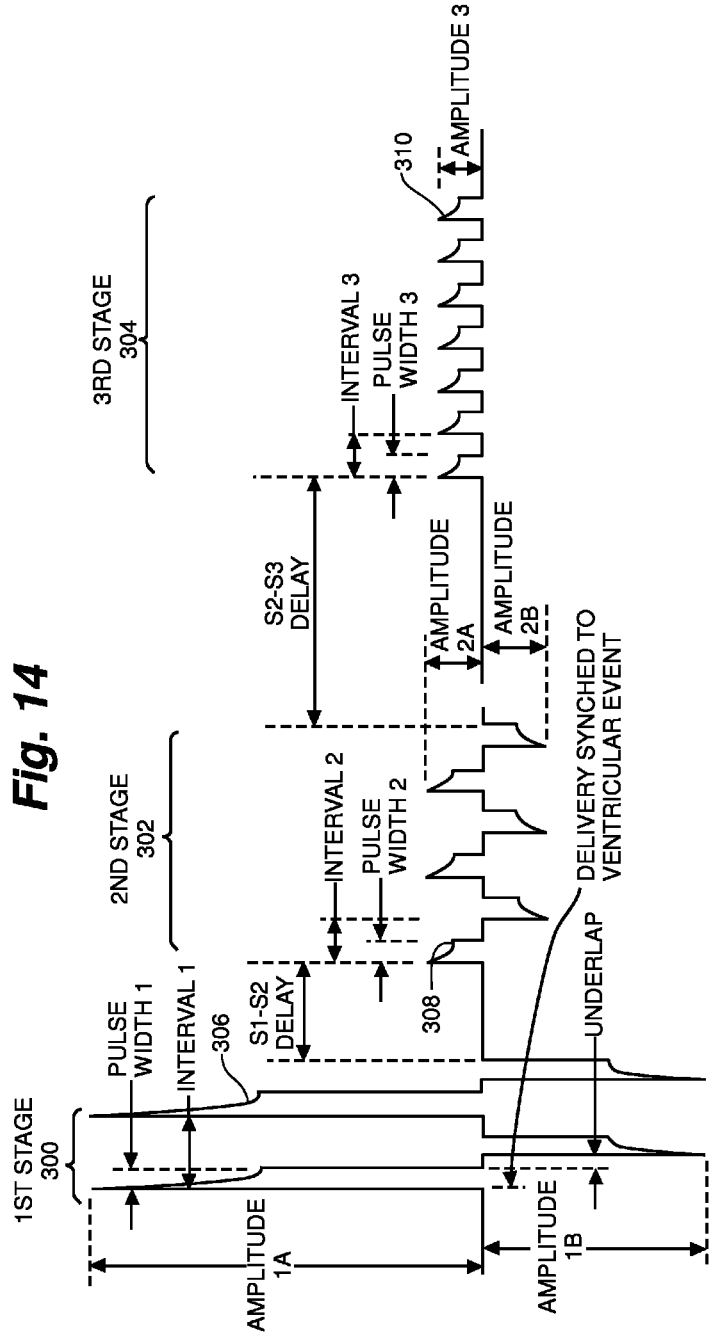
FIG. 14 depicts a three-stage therapy waveform.

Referring to FIG. 14, a low-energy, three-stage atrial defibrillation shock therapy (voltage vs. time) is depicted. The therapy includes three stages, a first stage 300, second stage 302, and third stage 304. First stage 300 comprises multiple "unpinning" pulses 306 intended to unpin a reentrant wave causing atrial fibrillation. As depicted, first stage 300 comprises two biphasic pulses, though first stage 300 could comprise more or fewer pulses, either monophasic or biphasic. Second stage 302 comprises multiple anti-repinning pulses 308 intended to prevent a reentrant wave from becoming repinned to cardiac tissue after being unpinned during first stage 300. As depicted, second stage 302 includes three biphasic pulses, though second stage 302 could comprise fewer or more pulses, either monophasic or biphasic. Third stage 304 comprises multiple pacing pulses 310 as understood by those skilled in the art.

In an embodiment, first stage 300 is applied for unpinning of one or more singularities associated with an atrial arrhythmia. Second stage 302 is applied for anti-repinning of the one or more singularities associated with the atrial arrhythmia. Third stage 304 is applied for extinguishing of the one or more singularities associated with the atrial arrhythmia. In various embodiments, first stage 300 has at least two and less than ten biphasic atrial cardioversion pulses of more than 10 volts and less than 100 volts with a pulse duration of approximately 3-4 milliseconds in some embodiments, or, more generally, of less than 10 milliseconds in various other embodiments, and a pulse coupling interval of between 20 to 50 milliseconds. In some embodiments, the first stage 300 has a total duration of less than two cycle lengths of the atrial arrhythmia and is delivered within a ventricular refractory period with an energy of each biphasic atrial cardioversion pulse less than 0.1 joules. An interstage delay (11) of between 100 to 300 milliseconds precedes the second stage 302. In some embodiments, the second stage 302 has at least two and less than ten far field pulses of less than ventricular far-field excitation threshold (10 volts) with a pulse duration of more than 5 and less than 20 milliseconds and a pulse coupling interval of between 70-90% of the cycle length of the atrial arrhythmia. An interstage delay (12) of between 100 to 300 milliseconds precedes the third stage 304. In some embodiments, the third stage 304 has at least five and less than ten near field pulses of less than 10 volts with a pulse duration of more than 0.2 and less than 5 milliseconds and a pulse coupling interval of between 70-90% of the cycle length of the atrial arrhythmia. In an embodiment, the three-stage atrial cardioversion therapy is delivered in response to detection of the atrial arrhythmia with each stage (300, 302 and 304) without confirmation of conversion of the atrial arrhythmia until after delivery of the third stage 304.

Implantable devices of the present invention as described above are capable of producing nearly any pulse shape, including ascending or descending shaped pulses at a lower overall energy as compared to traditional contiguous pulses. As such, the three-stage defibrillation therapy as depicted in FIG. 14, and other multi-stage therapies, may be improved upon through lowering of overall energy delivered, thereby reducing pain, and by creating ideal pulse shapes that may be more efficiently absorbed by cell membranes. Variations of improved three-stage therapies of the present invention are depicted in FIGS. 15-19.

FIG. 15 depicts a multi-stage therapy that includes first stage 400, second stage 402, and third stage 404. Although depicted as having three stages, it will be understood that other therapies may include more or fewer stages. In this embodiment, all stages include multiple pulses, which in an embodiment, may range from two to ten pulses, though fewer or more pulses per stage may be used in alternative embodiments.

As depicted, first stage 400 includes multiple biphasic pulses 406. Each biphasic pulse 406 comprises a first, positive pulse phase 406a and a second, negative pulse phase 406b. Pulse phase 406a comprises multiple sub-pulses 408a; pulse phase 406b comprises multiple sub-pulses 408b. In this embodiment, sub-pulses 408a and 408b may be considered monophasic pulse phases as their polarity within a given pulse phase is generally all positive or all negative. As will be discussed below with respect to FIG. 19, sub-pulses may be biphasic in that they switch polarity within a single pulse phase.

Further, as depicted, each individual sub-pulse has an initial voltage amplitude that is greater than its final voltage amplitude, reflecting the natural decay of delivery capacitor 112. In other therapy generation and deliver circuits, the shape of sub-pulses 408 may differ from the concave, decaying sub-pulse waveform depicted.

In the depicted therapy embodiment, sub-pulses 408a consecutively rise in voltage amplitude as they form the first phase of a pulse 406a. As such, in the depicted embodiment, sub-pulses 408a form an ascending, generally linear waveform, or pulse 406.

During a first phase, first stage sub-pulses 408a rise in amplitude from $V_{L1}$ to $V_{H1}$, which in an embodiment is 40V to 50V; during a second phase, sub-pulses 408b rise in amplitude from $-V_{L1}$ to $-V_{H1}$, which in an embodiment may be −30V to −40V.

As described above, sub-pulses may be used to form a variety of shaped pulses, not limited to ascending, ramped, or linear pulse or wave shapes, as will be depicted and described with respect to FIGS. 16-19.

In an embodiment, sub-pulses are delivered at a frequency of 50 kHz to 500 kHz, or in another embodiment, ranging from 100 kHz to 200 kHz. The frequency of sub-pulses may vary within a given pulse, pulse phase, stage, or therapy. In an embodiment, a duty cycle of the sub-pulses is 50%, such that the sub-pulse width is approximately equal to the time between sub-pulses. However, this duty cycle can change as needed, such as the case wherein a greater time between pulses is desirable to allow energy to transmit through tissue.

It will be noted that the sub-pulse widths (durations) are not drawn to scale in the figures. In an embodiment wherein a first phase 406a has a pulse width of 6 ms, and a sub-pulse duration of 20 μs (50 kHz frequency, 50% duty cycle), first phase 406a includes approximately 150 sub-pulses, which is graphically difficult to depict.

Second stage 402 in this embodiment also includes multiple biphasic pulses, pulses 410. Each pulse 410 includes a first pulse phase 410a and a second pulse phase 410b. Each pulse 410 comprises multiple sub-pulses 412. In this embodiment, second stage 402 pulses 410 are substantially similar to first stage 400 pulses 406 in that sub-pulses 412 form an ascending, linear pulse shape.

Third stage 404 may be similar in composition to first stage 400 and second stage 402 in that it comprises multiple pulses comprised of multiple sub-pulses, as generated by circuits of the present invention. However, in some embodiments, and as depicted, conventional pacing pulses 414 may be used as generated from conventional circuitry that may be integral to the therapy generation device of the present invention, and described above with respect to FIG. 1.

It will also be understood that although the pulse and sub-pulse shapes from first stage to second stage may be depicted as being similar, in other embodiments, pulse shapes may differ from stage to stage, and even from pulse to pulse within a stage.

Referring to FIG. 16, an alternate embodiment of a multi-stage, pulse-shaped waveform therapy is depicted. The therapy of FIG. 16 is substantially the same as the therapy of FIG. 15, with the exception of FIG. 16 including only monophasic pulses.

In this embodiment, the depicted atrial therapy includes first stage 420 comprising two monophasic pulses 422; second stage 424 comprising five monophasic pulses 426; and third stage 428 comprising seven conventional pacing pulses 430.

First stage 420 shaped pulses 422 include multiple ascending sub-pulses 432 rising from $V_{L1}$ to $V_{H1}$; second stage 424 sub-pulses 434 rise from $V_{L2}$ to $V_{H2}$.

Referring to FIG. 17, another embodiment of a multi-stage, pulse-shaped waveform therapy is depicted. In this embodiment, the therapy is substantially the same as the therapy of FIG. 16, with the exception that sub-pulse amplitudes decrease in a non-linear manner.

In this embodiment, the depicted atrial therapy includes first stage 440 comprising two monophasic pulses 442; second stage 444 comprising five monophasic pulses 446; and third stage 448 comprising seven conventional pacing pulses 450.

First stage 440 shaped pulses 442 include multiple ascending sub-pulses 452 rising from $V_{L1}$ to $V_{H1}$; second stage 424 sub-pulses 454 rise from $V_{L2}$ to $V_{H2}$.

Referring to FIG. 18, another embodiment of a multi-stage, pulse-shaped waveform therapy is depicted. In this embodiment, therapy sub-pulses within a single pulse rise initially to a peak, then fall.

In this embodiment, the depicted atrial therapy includes first stage 460 comprising two monophasic pulses 462; second stage 464 comprising seven monophasic pulses 466; and third stage 468 comprising seven conventional pacing pulses 470.

First stage 460 shaped pulses 462 include multiple ascending sub-pulses 472 rising from $V_{L1}$ to $V_{H1}$, then falling from $V_{H1}$ back to $V_{L1}$; second stage 464 sub-pulses 474 rise from $V_{L2}$ to $V_{H2}$, then fall to $V_{L2}$.

Referring to FIG. 19, another embodiment of a multi-stage, pulse-shaped waveform therapy is depicted. In this embodiment, each sub-pulse comprises a biphasic waveform.

In this embodiment, the depicted therapy includes first stage 480 comprising three pulses 482, second stage 484 comprising eight pulses 486, and third stage 488 comprising eight pulses 490.

First stage 460 shaped pulses 482 comprise multiple biphasic sub-pulses 492 having a first phase 492a and a second phase 492b; second stage 484 also includes multiple biphasic sub-pulses, sub-pulses 494 having first phase 494a and second phase 494b.

It will be understood that a variety of biphasic and monophasic sub-pulses may be used within a single pulse or within a stage or therapy to form unique therapies according to embodiments of the present invention.

Although the present invention has been described with respect to the various embodiments, it will be understood that numerous insubstantial changes in configuration, arrangement or appearance of the elements of the present invention can be made without departing from the intended scope of the present invention. Accordingly, it is intended that the scope of the present invention be determined by the claims as set forth.

For purposes of interpreting the claims for the present invention, it is expressly intended that the provisions of Section 112, sixth paragraph of 35 U.S.C. are not to be invoked unless the specific terms "means for" or "step for" are recited in a claim.

What is claimed is:

1. An atrial arrhythmia treatment apparatus, comprising:
at least one electrode adapted to be implanted proximate an atrium of a heart of a patient to deliver pulses;
at least one electrode adapted to be implanted proximate the atrium of the heart of the patient to deliver near field pulses and sense cardiac signals;
an implantable therapy generator adapted to be implanted in a patient and operably connected to the electrodes, including:
sensing circuitry that senses cardiac signals representative of atrial activity and ventricular activity;
detection circuitry operably connected to the sensing circuitry to evaluate the cardiac signals representative of atrial activity to determine an atrial cycle length and detect an atrial arrhythmia based at least in part on the atrial cycle length;

control circuitry operably connected to the sensing circuitry that, in response to the atrial arrhythmia, controls generation and selective delivery of a multi-stage atrial cardioversion therapy to the electrodes, each stage comprising a plurality of pulses, each pulse comprising a plurality of high-frequency sub-pulses; and therapy circuitry operably connected to the electrodes and the control circuitry including:
  a high-voltage charging circuit in electrical connection with a storage capacitor, the high-voltage charging circuit adapted to charge the storage capacitor to a predetermined voltage;
  a delivery capacitor connectable to the storage capacitor and to the at least one electrode adapted to be implanted proximate the atrium of the heart;
  a control circuit adapted to selectively cause the storage capacitor to be electrically connected to the delivery capacitor so as to charge the delivery capacitor to a predetermined delivery voltage, and to cause a delivery switching circuit to be repeatedly opened and closed at a predetermined rate, thereby electrically connecting and disconnecting the delivery capacitor to the at least one electrode to be implanted proximate the atrium of the heart such that multiple electrical sub-pulse shocks are transmitted to the at least one electrode to be implanted proximate the atrium of the heart.

2. A method of treating atrial arrhythmias comprising:
(a) providing an atrial arrhythmia treatment device including a therapy generator adapted to generate and selectively deliver a multi-stage atrial cardioversion therapy and at least two leads operably connected to the therapy generator, each lead having at least one electrode adapted to be positioned proximate the atrium of a heart of the patient;
(b) providing instructions for implanting the atrial arrhythmia treatment device in a patient during a surgical procedure;
(c) providing instructions for configuring the atrial arrhythmia treatment device at a time after completion of the surgical procedure, including instructions for programming the atrial arrhythmia treatment device with a set of therapy parameters for delivering the multi-stage atrial cardioversion therapy to a patient via both a far-field configuration and a near-field configuration of the electrodes upon detection of an atrial arrhythmia by the atrial arrhythmia treatment device,
wherein each stage of the multi-stage atrial cardioversion therapy includes at least two and less than ten atrial cardioversion pulses of more than 10 volts and less than 500 volts with a pulse duration of less than 10 milliseconds, each pulse comprising multiple sub-pulses having a sub-pulse duration of less than 20 microseconds.

* * * * *